United States Patent
Weimbs et al.

(10) Patent No.: US 11,013,705 B2
(45) Date of Patent: May 25, 2021

(54) METHODS AND COMPOSITIONS FOR SUPPORTING RENAL HEALTH

(71) Applicants: The Regents of the University of California, Oakland, CA (US); Augusta University Research Institute, Augusta, GA (US)

(72) Inventors: Thomas Weimbs, Santa Barbara, CA (US); Jacob Torres, Santa Barbara, CA (US); Muthusamy Thangaraju, Evans, GA (US)

(73) Assignees: The Regents of the University of California, Oakland, CA (US); Augusta University Research Institute, Augusta, GA (US)

( * ) Notice: Subject to any disclaimer, the term of this patent is extended or adjusted under 35 U.S.C. 154(b) by 0 days.

(21) Appl. No.: 16/819,079

(22) Filed: Mar. 14, 2020

(65) Prior Publication Data

US 2020/0289444 A1     Sep. 17, 2020

Related U.S. Application Data

(60) Provisional application No. 62/818,538, filed on Mar. 14, 2019.

(51) Int. Cl.
| | |
|---|---|
| *A61K 31/194* | (2006.01) |
| *A61P 13/12* | (2006.01) |
| *A23L 33/20* | (2016.01) |
| *A61K 31/047* | (2006.01) |

(52) U.S. Cl.
CPC .......... *A61K 31/194* (2013.01); *A23L 33/20* (2016.08); *A61K 31/047* (2013.01); *A61P 13/12* (2018.01)

(58) Field of Classification Search
CPC ...... A61P 13/12; A61K 31/194; A61K 31/047
See application file for complete search history.

(56) References Cited

U.S. PATENT DOCUMENTS

| | | | |
|---|---|---|---|
| 5,693,850 A | 12/1997 | Birkhahn et al. | |
| 9,675,577 B2 | 6/2017 | D'Agostino et al. | |
| 9,795,580 B2 | 10/2017 | Weeber et al. | |
| 9,993,555 B2* | 6/2018 | Akers | A61K 47/12 |
| 10,051,880 B2 | 8/2018 | Clarke et al. | |
| 10,376,528 B2 | 8/2019 | Schmidt | |
| 10,559,258 B2 | 2/2020 | Hu | |
| 2006/0083727 A1 | 4/2006 | Kajander et al. | |
| 2009/0247589 A1* | 10/2009 | Zandi-Nejad | A61P 37/06 514/356 |
| 2015/0297545 A1 | 10/2015 | Rimer et al. | |
| 2018/0318280 A1 | 11/2018 | Ammer | |
| 2019/0060415 A1 | 2/2019 | Bellamine | |

FOREIGN PATENT DOCUMENTS

| | | |
|---|---|---|
| EP | 1661574 B1 | 5/2006 |
| WO | 2008033352 A2 | 4/2008 |
| WO | 2011057110 A1 | 5/2011 |
| WO | 2019018683 A1 | 1/2019 |
| WO | 2018187852 A1 | 10/2019 |

OTHER PUBLICATIONS

Grundmann et al., Preoperative Short-Term Calorie Restriction for Prevention of Acute Kidney Injury After Cardiac Surgery: A Randomized, Controlled, Open-Label, Pilot Trial. J Am Heart Assoc 7, (2018.).
Goldberg et al., Ketogenic diet activates protective γδ T cell responses against influenza virus infection. Science Immunology, 2019; 4 (41): eaav2026.
Tanner and Tanner, Dietary Citrate Treatment of Polycystic Kidney Disease in Rats Nephron Physiol 2003;93:p. 14-p. 20.
Tanner, Tanner, Potassium citrate/citric acid intake improves renal function in rats with polycystic kidney disease, JASN Jul. 1998, 9 (7) 1242-1248.
International Search Report (from a corresponding foreign application), PCT/US2020/022619, dated Jul. 8, 2020.
International Search Report (from a corresponding foreign application), PCT/US2020/022619, dated 2020.

* cited by examiner

*Primary Examiner* — Marcos L Sznaidman

(57) ABSTRACT

Compositions and methods for supporting health, especially renal health, comprising ketonic agents that recapitulate beneficial effects of ketosis by exogenously administered agents. The agents include BHB, analogs thereof, and GPR109A agonists. The agents may further include crystal precipitation inhibitors which synergistically improve treatment of certain renal conditions. The agents may be used in dietary supplements and therapeutic compositions for the treatment of cystic kidney diseases such as polycystic kidney disease, ciliopathies, and other conditions.

14 Claims, 11 Drawing Sheets

METHODS AND COMPOSITIONS FOR SUPPORTING RENAL HEALTH

CROSS-REFERENCE TO RELATED APPLICATIONS

This application claims the benefit of priority to U.S. Provisional Patent Application Ser. No. 62/818,538 entitled "BHB and BHB-Citrate Combination Therapy for Polycystic Kidney Disease," filed Mar. 14, 2019 the contents of which are hereby incorporated by reference.

STATEMENT REGARDING FEDERALLY SPONSORED RESEARCH OR DEVELOPMENT

This invention was made with government support under grant number R01-DK109563 awarded by the National Institutes of Health. The government has certain rights in the invention.

BACKGROUND OF THE INVENTION

Renal disease is a major health issue. Among the various renal conditions that afflict people, renal cysts are present in numerous pathologies of the kidney. Polycystic kidney disease (PKD) is an especially serious condition with high morbidity and mortality. Autosomal dominant polycystic kidney disease (ADPKD) is considered the most common life-threatening monogenic disease. The PKD disease state is characterized by the growth of fluid-filled cysts in the kidneys which progressively enlarge, leading to destruction of normal renal tissue and function. Renal cyst growth in PKD is driven by several growth factors, hormones and cytokines that are present in the cyst fluid and which stimulate the cyst-lining epithelial cells. In the United States, the only FDA-approved therapeutic for ADPKD is the vasopressin receptor 2 antagonist tolvaptan. Its use is complicated due to significant side effects and potential toxicities, poor cost-effectiveness and questions potentially limited efficacy. Accordingly, there remains a need in the art for effective ways of preventing and treating renal conditions, including cystic renal conditions such as polycystic kidney disease.

Polycystic kidney disease is one of several pathological conditions classified as a ciliopathy. Cilia are microtubule-containing structures that protrude from the surface of most cells types. Cilia, especially immotile primary cilia, act as a "cellular antenna" with various functions including sensory and cell-to-cell communication roles. Many pathological conditions are associated with mutations that result in abnormal cilial formation or function. There are over 35 known ciliopathies, and for many of these conditions, effective treatments are not available. Accordingly, there remains a need in the art for novel ways of preventing and ameliorating ciliopathies.

Meanwhile, the metabolic state of ketosis is a growing area of study. Ketosis is characterized by elevated abundance of ketone bodies in blood and other compartments. Ketosis is a metabolic pathway induced by low glucose conditions, for example, being induced by low-carbohydrate diet or fasting. Numerous health benefits appear to be associated with dietary ketosis, including weight loss and appetite control, improved cholesterol status, and stabilization of blood glucose and insulin. The use of ketogenic diets has been applied to control epilepsy in children and blood glucose in Type 2 diabetics. It is thought that ketogenic diets may be of benefit in addressing many other conditions, for example, in the context of kidney injury in surgical subjects, caloric restriction was found to have protective effect on renal function, as described in Grundmann et al., Preoperative Short-Term Calorie Restriction for Prevention of Acute Kidney Injury After Cardiac Surgery: A Randomized, Controlled, Open-Label. Pilot Trial. *J Am Heart Assoc* 7, (2018.) However, the mechanisms by which ketosis acts on pathological processes and conditions is not well understood, and previously recognized dietary benefits have not been translated to practical applications and interventions. Accordingly, there is a need in the art for an improved understanding of the molecular signaling mechanisms or other physiological effects by which ketosis achieves health benefits. Furthermore, long-term adherence to ketogenic diets is difficult and compliance is poor for many, if not most, subjects. Accordingly, there is further need in the art for novel therapies that harness the beneficial effects of ketosis while being readily administered or applied.

SUMMARY OF THE INVENTION

By various novel discoveries, the inventors of the present disclosure have provided the art with novel compositions of matter and methods for improving health and preventing and treating disease. The inventors of the present disclosure have elucidated that beta hydroxybutyrate (BHB), produced in dietary ketosis, activates certain beneficial pathways and processes. Among these, the activation of GPR109A by BHB is shown herein to provide various therapeutic effects. Based on these discoveries, the inventors of the present disclosure have identified and developed compositions with beneficial and therapeutic properties, and methods of applying them.

In a first aspect, the scope of the invention encompasses novel compositions for promoting health, preventing disease, and treating pathological conditions. These compositions, termed "ketonic compositions" herein, comprise BHB, BHB precursors that convert to BHB in vivo, BHB-like molecules, and functional mimics of BHB, including chemically unrelated species, that recapitulate the beneficial signaling activities of BHB.

Advantageously, the ketonic compositions can be formulated as dietary supplements, for convenient oral administration. In many cases, the ketonic compositions comprise inexpensive off-the-shelf ingredients with long-established safety profiles, and thus can be provided without the need for clinical trials, and may be utilized without the need for a prescription.

In another aspect, by the discoveries herein, the scope of the invention encompasses novel uses of GPR109A agonists. Many such agents have been previously developed and clinically investigated for other purposes, and may be repurposed in the methods of the invention for novel therapeutic applications.

In another aspect, the scope of the invention encompasses novel compositions and methods for improving renal health, and preventing and treating various conditions of the kidney. In one aspect, the inventions disclosed herein are advantageously applied for subjects at risk of or suffering from various renal cystic conditions, especially polycystic kidney disease. The scope of the invention encompasses dietary supplements and uses thereof for promoting renal health by preventing the formation of cysts and selectively destroying cyst epithelial cells.

Likewise, in another novel use, ketonic agents may be used to prevent or ameliorate the severity of acute kidney injury, for example, being used as preventative agents prior to surgery to reduce the risk or severity of acute kidney injury associated with surgery. In another novel use, ketonic agents may be used to ameliorate the risk or severity of ischemic perfusion injury, for example, as preventative, e.g., presurgical treatments.

In another aspect, the inventors of the present disclosure have determined that the ketonic agents of the invention may be combined with crystal precipitation inhibitors with synergistic beneficial activity. By preventing the formation of calcium, oxalate, or uric acid crystals, which underlie or exacerbate the pathology of various renal conditions such as cysts, acute kidney injury, and reperfusion injury, the combination products of the invention provide enhanced preventative and therapeutic effects. Specifically, citrate, a safe and readily available ingredient, is a crystal precipitation inhibitor that can be combined with ketonic agents, for example, in dietary supplements.

In another aspect, the inventors of the present disclosure have developed novel compositions of matter comprising bi-functional molecules made up of a ketonic agent and a crystal precipitation inhibitor, for example, a BHB-citrate combined molecule. These novel combination products provide the art with synergistic beneficial effects from a single agent having favorable formulation and administration properties.

In another aspect, the inventors of the present disclosure have determined that cystic epithelial cells are metabolically inflexible, being dependent upon glucose and being unable to metabolize fatty acids. Accordingly, in one aspect, the scope of the invention encompasses novel combination products made up of ketonic agents in combination with compositions that are lipotoxic to pathological cells such as polycystic kidney cyst epithelial cells and other undesirable cell types. The co-administration of ketonic agents and lipotoxic compositions provides enhanced preventatives and treatments for PKD cysts and other conditions.

In another aspect, the scope of the invention encompasses novel means of preventing and treating ciliopathies. The ketonic compositions of the invention, including exogenous ketones and GPR109A agonists, may be utilized in dietary supplements and therapeutic compositions for ameliorating the risk, onset, and severity of numerous ciliopathies such as PKD and retinitis pigmentosa.

These various inventions, and other beneficial applications of the discoveries disclosed herein, address a number of unmet needs in the art, as described in more detail in the sections that follow.

BRIEF DESCRIPTION OF THE DRAWINGS

FIG. 2A depicts the cystic index (percent cystic area) for kidneys of rats on the TRF or AL diet. FIG. 2B depicts the total number of cysts per kidney section in AL and TRF animals. FIG. 2C depicts cyst sizes of the cysts counted in 2B.

FIG. 4A depicts the cystic index (percent cystic area) from NC (normal chow) and KD (keto diet) cystic rats. [Dr6] FIG. 4B depicts serum creatinine. FIG. 4C depicts total number of cysts per kidney section. FIG. 4D depicts the size of cysts counted in FIG. 4C. FIG. 4E depicts quantification of pS6-positive cells in cyst-lining epithelia as a percent of the total number of DAPI-stained nuclei in cysts. Error bars represent SD. Statistical significance determined from Mann-Whitney analysis. n=8 male and 7 female Cy+ rats; n=13 male and 6 female wild-type rats for ketogenic diet experiments ($*p<0.05$, $****p<0.0001$).

FIG. 5A depicts Cystic index (percent cystic area). FIG. 5B depicts the total number of cysts per kidney section. FIG. 5C depicts the size of cysts counted in FIG. 5B.

FIG. 6A depicts blood BHB levels in male rats. FIG. 6B depicts blood BHB levels in female rats. FIG. 6C depicts cystic index (percent cystic area) in kidneys of fasted PKD rats.

FIG. 8A depicts 2-kidney to total body weight ratio in wild type (WT) and Cy+ PKD rats. FIG. 8B depicts cystic area (percent cystic area) in kidneys of the treated PKD rats.

DETAILED DESCRIPTION OF THE INVENTION

Figure 1:
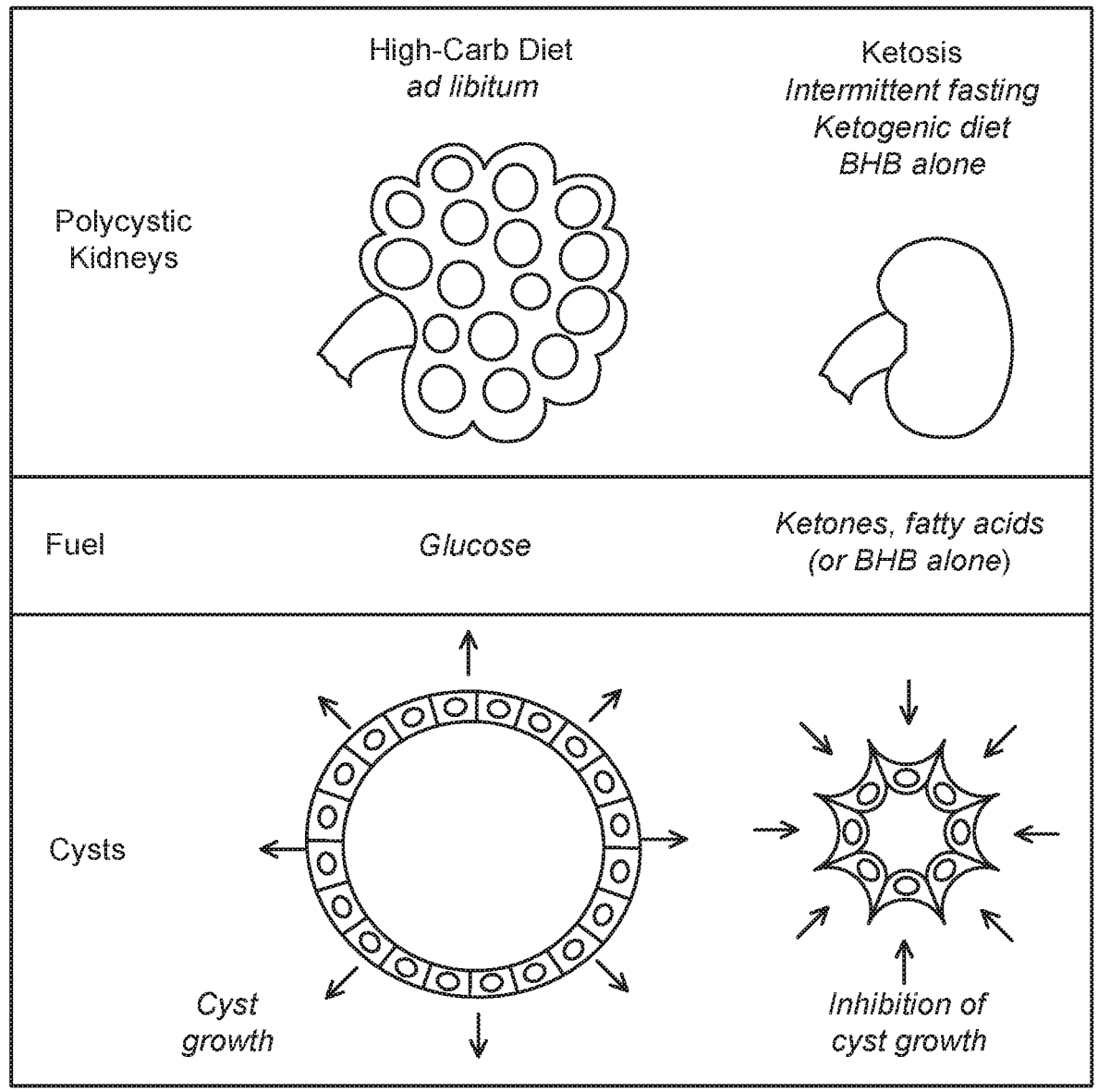
FIG. 1 is a diagrammatic representation of the effects of a ketogenic diet or the application of ketonic compositions on polycystic kidneys. Without intervention, kidneys are ridden with cysts and cysts expand (left). With sufficient intervention, cysts are reduced and kidneys return towards normal condition (right).

The various inventions disclosed herein are directed to dietary supplements, pharmaceutical compositions, and other compositions comprising BHB or BHB-related compounds, and the novel uses of such compositions in maintaining health, preventing disease and treating various conditions. In a primary embodiment, the support of kidney health and the treatment of kidney disease is encompassed by the compositions and methods of the invention, for example, the treatment of polycystic kidney disease.

Part 1. Compositions of the Invention

In a first aspect, the scope of the invention encompasses compositions which may be used to promote wellness, prevent disease, or treat various conditions. The compositions of the invention encompass BHB and other ketone bodies and variants thereof as well as unrelated chemical structures which functionally recapitulate the biological and therapeutic effects of BHB. Therefore, the compositions of the invention will be referred to herein broadly as "ketonic compositions." As set forth below, the ketonic compositions of the invention may comprise any number of ketone bodies, ketone body precursors, ketone body functional mimics, and multifunctional combination products comprising two or more ketone bodies or analogs. In some implementations, the scope of the invention encompasses multifunctional combination products comprising ketone bodies or analogs with additional functional agents that augment or synergize the benefits of the ketones. In some embodiments, the ketonic compositions of the invention comprise novel compositions of matter. In some embodiments, the ketonic compositions of the invention comprise known compositions of matter that are repurposed for novel uses.

Ketosis Mimic.

In a first aspect, the ketonic composition of the invention encompasses a ketosis mimic. As used herein, a ketosis mimic is a composition of matter which, when administered to a subject, induces or recapitulates, in whole or in part, processes or states active in ketosis, for example, dietary ketosis, i.e. ketosis induced by fasting or otherwise restricting glucose, for example, a blood ketone level of 0.5 mM or greater.

In one aspect, the ketosis mimic may comprise an exogenous ketone. An exogenous ketone is an exogenously applied ketone body that is structurally or functionally like BHB or other ketone bodies found circulating in subjects experiencing ketosis, e.g. dietary ketosis, or which is converted to a ketone body in vivo.

BHB and BHB Analogs.

In a primary implementation, the ketosis mimic is BHB or a BHB analog. As known in the art, beta-hydroxybutyric acid, abbreviated BHB, is a ketone that is synthesized in the liver from acetyl-CoA formed from the breakdown of fatty acids via several intermediates and reaction steps. BHB is formed in ketosis or other low glucose conditions. STRUCTURE 1:

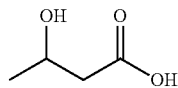

For example, BHB may be employed either as the free acid or as a salt or a mixture of both. BHB or BHB salts are preferentially administered in oral formulations for gastrointestinal absorption leading to distribution via the circulation and effects of BHB in the body including the kidneys.

Likewise, analogs of BHB may also be employed in the compositions and methods of the invention. Direct administration BHB in its free acid form may be problematic due to its acidity. Likewise, administration of BHB salts may be problematic due to increased salt intake which may be undesired. Accordingly, in various implementations, a composition that is converted to BHB in vivo or which mimics BHB may be used in place of free BHB or BHB salts. As used herein, "BHB analogs" broadly encompasses compositions that (1) are converted to BHB in vivo or (2) have structural similarly to BHB and promote like physiological responses as those promoted by BHB.

In one embodiment, the BHB analog is a precursor of BHB. A BHB precursor is a composition that is converted to BHB in vivo via one or more reactions or intermediates. In one embodiment, the BHB precursor is butyrate. In one embodiment, the BHB precursor is beta-hydroxy beta-methylbutyrate. In one embodiment, the BHB precursor is a ketogenic amino acid or a deaminated keto-analogue of a ketogenic amino acid. In one embodiment, the BHB precursor is acetoacetate (the physiological form of acetoacetic acid). In one embodiment, the BHB precursor is poly-beta-hydroxybutyrate. In one embodiment, the BHB precursor is beta-hydroxybutyryloxy-butyrate.

In one embodiment, the BHB precursor is 1,3 butanediol, Structure 2:

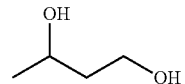

1,3 butanediol is water soluble and well tolerated by animals, including humans. In the body, it is efficiently converted to BHB by enzymatic and/or chemical action, for example, wherein alcohol dehydrogenase catalyzes metabolism of 1,3-butanediol to beta-hydroxybutyraldehyde, which is subsequently oxidized to beta-hydroxybutyrate by aldehyde dehydrogenase. Advantageously, 1,3 butane diol is neutral and can be administered directly without the need to formulate as a salt. In one embodiment, the BHB precursor is 1,3-butanediol diacetoacetate. 1,3-butanediol diacetoacetate is water soluble, well tolerated in animals and converted to BHB in vivo.

In one embodiment, the BHB analog comprises a BHB precursor comprising a fat molecule which is readily converted to ketones in the body. In one embodiment, the BHB precursor is a medium chain triglyceride (MCT), for example, a triglyceride comprising six to 12 carbon chains. MCTs are more efficiently converted to ketones in vivo than shorter or longer chain fats. Exemplary MCTs include caproic acid (C6), caprylic acid (C8), capric acid (C10), and lauric acid (C12).

BHB Esters. The BHB analogs of the invention further encompass esters of BHB, and esters of BHB analogs, wherein the oxygen of the hydroxyl group of the BHB carboxylic acid moiety (carbon 1) is conjugated with a hydroxyl group of another compound. Exemplary esters include methyl, ethyl, propyl (e.g. n-propyl or 2-propyl), butyl (e.g. tert-butyl), pentyl, hydroxylbutyl, hydroxylpropyl, glycerol, citrate, or glycol groups joined to the 1 carbon of BHB. Other exemplary esters are 3-hydroxybutyrate-(R)-1,3-butanediol monoester. Esters of BHB at the 1 carbon eliminate the carboxylic acid group and associated charge. In vivo, these compositions are de-esterified by esterase enzymes, releasing BHB (or the BHB analog or mimic in some cases). Such compositions may have improved solubility, increased membrane permeability, improved stability, more sustained release, and increased tolerance compared to native BHB or BHB analogs. Reference to "BHB" and "BHB analogs" herein will be understood to encompass esters of BHB and esters of BHB precursors and mimic compositions. Esters of the 3 carbon are also within the scope of the invention.

Various BHB esters are known in the art. Additional BHB esters may include compositions of the formula: STRUCTURE 3

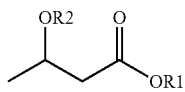

wherein R1 and/or R2 may be an alkyl moiety, for example, comprising one to twelve carbons, for example, methyl, ethyl, propyl (e.g. n-propyl or 2-propyl), butyl (e.g. tert-butyl), pentyl, hydroxylbutyl, hydroxylpropyl, glycerol, citrate, or glycol.

In some embodiments the BHB analog is a polymer of BHB or a polymer of a BHB analog. One example is polymeric BHB which is a polymeric ester between the carboxyl group of BHB and the hydroxyl group of BHB. Hydrolysis of polymeric BHB, for example in the gastrointestinal tract, either chemically, enzymatically or mediated by microorganisms, may lead to release of monomeric BHB and uptake into circulation.

In some embodiments, the therapeutic composition of the invention comprises a BHB prodrug, or BHB analog prodrug. A BHB prodrug, or BHB analog prodrug, is a composition comprising a cleavable promoiety conjugated to BHB, or a BHB analog. In the body of a subject to which the prodrug is administered, the promoiety is cleaved by enzymatic or chemical action to release the BHB, or BHB analog. In a primary embodiment, the promoiety is joined to the BHB or BHB analog by ester linkage to the 1 and/or 3 carbon.

Various BHB analogs, including BHB esters and oligomers, are known in the art. Any such compositions may be selected as the ketonic composition of the invention. In one embodiment, the BHB analog comprises 3-hydroxybutyl 3-hydroxybutyrate, as described in U.S. Pat. No. 10,051,880, Hydroxybutyrate ester and medical uses thereof, by Clarke and Veech. In one embodiment, the BHB analog comprises R,S-1,3-butanediol acetoacetate, for example, as described in U.S. Pat. No. 9,795,590, Ketone supplements for treatment of angelman syndrome, by Weeber et al. In one embodiment, the BHB analog is an oligomer of (R)-3-hydroxybutyrate, for example, as described in U.S. Pat. No. 10,559,258, Nutritional supplements and therapeutic compositions comprising (R)-3-hydroxybutyrate derivatives, by Veech and King. The BHB analog may comprise a composition described in U.S. Pat. No. 10,376,528, Composition comprising ketone body and nicotinamide adenine dinucleotide modulator and methyl donor, by Schmidt or in U.S. Pat. No. 5,693,850, Nutritive water soluble glycerol esters of hydroxy butyric acid, by Birkhahn et al.

Enantiomers.

BHB is a chiral composition having two enantiomers: D-β-hydroxybutyric acid (also known as R-β-hydroxybutyric acid) and L-β-hydroxybutyric acid (also known as S-3-hydroxybutyric acid). The D- and L-forms of BHB are determined by the tetrahedral orientation of the hydroxyl group (or oxy group, in BHB esters) on the third carbon of BHB. D-BHB is the most common endogenous form of BHB. L-BHB is only occurring in small amounts in cells, and thus is metabolized or cleared at a slower rate, while retaining key signaling properties of endogenous D-BHB.

Reference to "BHB" or a "BHB analog" made herein will be understood to encompass any mixture of D-BHB and L-BHB isoforms, unless the proportion of the enantiomers is specifically specified. Exemplary mixtures of enantiomers include substantially pure formulations of D-BHB and D-BHB analogs, for example, formulations comprising at least 80%, at least 85%, at least 90%, at least 95%, at least 96%, at least 97%, at least 98%, or at least 99% D-BHB or a D-BHB analog. Likewise, the mixture of enantiomers may comprise a substantially pure formulation of L-BHB or a L-BHB analog, for example, formulations comprising at least 80%, at least 85%, at least 90%, at least 95%, at least 96%, at least 97%, at least 98%, or at least 99% L-BHB or L-BHB analog. In other embodiments, the percentage of D-BHB or D-BHB analog in the mixture may be at least 5%, 10%, 15%, 20%, 25%, 30%, 35%, 40%, 45%, 50% (racemic mixture), 55%, 60%, 65%, 70%, 75%, 80%, 85%, 90%, or 95%.

GPR109A Activators. In one aspect, the ketonic compositions of the invention will comprise an activator of GPR109A. GPR109A, also known as hydroxycarboxylic acid receptor 2 (HCA2), and niacin receptor 1 (NIACR1 in humans) is a hydroxycarboxylic acid receptor. In humans, GPR109A is encoded by the HCAR2 gene. As used herein, a GPR109A agonist or activator is a composition which activates, i.e. increases the activity of, GPR109A. In one embodiment, GPR109A activation is indicated by a reduction in intracellular cAMP concentration. In one embodiment, GPR109A activation is indicated by a reduction in lipolysis. Activation of GPR109a occurs when a ligand or agonist binds to this receptor and causes a conformational change that then leads to activation of an associated heterotrimeric G-protein, in this case typically a Gi/Go-type G protein. The activated G protein then regulates subsequent intracellular signaling pathways such as the inhibition of adenylate cyclase leading to lowering of the intracellular cAMP concentration. Both, natural ligands—such as BHB—and artificial ligands—such as certain pharmacological compounds—can act as agonists of GPR109A.

In one embodiment, the GPR109A agonist is an exogenous ketone. The inventors of the present disclosure have unexpectedly determined that ketones present in ketosis have GPR109A activation activity and that this activity underlies various beneficial processes and effects of dietary ketosis. In one embodiment, the exogenous ketone is BHB or BHB analog, as described above.

In alternative implementations, the GPR109A agonist is a non-ketone. In one embodiment, the GPR109 agonist is niacin, or a niacin analog such as inositol nicotinate. It will be understood that niacin in small doses is not sufficient to significantly activate GPR109A, and that dosage forms of less than the minimal dose, or doses administered at less than the minimal activation dose will not be considered GPR109A activators. In one embodiment, the niacin or niacin mimic is provided (e.g. a dosage form) or administered in a biologically or therapeutically effective amount, being an amount sufficient to significantly activate GPR109A, for example, in various embodiments being at least 100 mg, 250 mg, at least 500 mg, at least 750 mg, at least 1 gram, or at least 1.5 gram, for example, in human subjects. In some embodiments, niacin provided or administered in a biologically or therapeutically effective amount comprising a megadose suitable for activation of GPR109A, for example, a dosage form or a daily administration of, for example 1 to 6 grams daily.

In various embodiments, the GPR109A agonist may be any of the following, as well as variants, derivatives, and polymorphs of the following. In one embodiment, the GPR109A agonist is GSK256073, for example, as described in Specher et al., 2015, Discovery and characterization of GSK256073, a non-flushing hydroxy-carboxylic acid receptor 2 (HCA2) agonist, Eur J Pharmacol 756: 1-7. In one embodiment, the GPR109A agonist is selected from the group consisting of (1aR,5aR) 1a,3,5,5a-Tetrahydro-1H-2,3-diaza-cyclopropa[a]pentalene-4-carboxylic Acid (MK-1903), monomethylfumarate acipimox, acifran, 3-pyridineacetic acid, 5-methylnicotinic acid, pyridazine-4-carboxylic acid pyrazine-2-carboxylic acid, LUF6281 and LUF6283, and a pyrazolyl propionyl cyclohexenamide, for example, as described in Ding et al., 2010, Discovery of pyrazolyl propionyl cyclohexenamide derivatives as full agonists for the high affinity niacin receptor GPR109A, Bioorg Med Chem Letters 21: 2721-2724. Palani et al., Discovery of SCH 900271, a Potent Nicotinic Acid Receptor Agonist for the Treatment of Dyslipidemia, ACS Med Chem Lett. 2012

3(1): 63-68. Additional GPR109 agonists include compositions described in PCT International Patent Application Publication Number WO2008051403, Acyl hydroxypyrazoles as novel agonists for high-affinity nicotinic acid receptor GPR109A, by Beresis and Colletti; U.S. Pat. No. 7,723,342, Heterocycles as nicotinic acid receptor agonists for the treatment of dyslipidemia, by Palani et al.; United States Patent Application Publication Number US20090062269, Niacin Receptor Agonists, Compositions Containing Such Compounds and Methods of Treatment, by Raghavan et al.

In one embodiment, the GPR109A agonist is 5-[3-(1-methylcyclopropyl)propyl]-1H,2H,3H,4H,7H-pyrano[2,3-d]pyrimidine-24,7-trione, also known as SCH900271, a nicotinic acid derivative known in the art for the treatment of dislipideima. In one embodiment, the GPR019 agonist is (4aR,5aR)-4,4a,5,5a-Tetrahydro-1H-cyclopropa[4,5]cyclopenta[1,2]pyrazole-3-carboxylic acid, also known as MK1903.

The present disclosure makes reference to the administration or ingestion of "a ketonic composition." It will be understood that reference to a ketonic composition encompasses "one or more" ketonic agents, for example, one ketonic agent or a combinations of two or more difference ketonic agents. Combinations of different ketonic agents may be utilized, for example having different ADMET properties or physiological effects, in order to optimize the delivery, distribution, and action of ingested or administered products or to broaden the therapeutic effects thereof.

Synergistic Combination Products.

The inventors of the present disclosure have advantageously determined that the efficacy of ketonic compositions such as BHB, BHB analogs, and GPR109A agonists is dramatically, and synergistically, enhanced when the agent is combined with a crystal precipitation inhibiting agent. The crystal precipitation inhibiting agent, as used herein, encompasses any agent that acts to inhibit the in vivo formation of crystals such as calcium or uric acid crystals. As is discussed below, in various contexts, crystal formation may be pathological or may promote pathological outcomes, for example, in the kidney. By inhibiting undesirable crystal precipitation, administration of the crystal precipitation-modulating compositions of the invention enhances the therapeutic effects of ketonic compositions such as BHB, BHB analogs, and GPR109A activators. In one aspect, the scope of the invention encompasses a novel combination product comprising a ketonic composition and a crystal precipitation inhibitor, e.g. BHB or a BHB analog (such as a BHB precursor) in combination with the crystal precipitation inhibitor. In a related embodiment, the scope of the invention encompasses methods of supporting health, e.g. renal health, or treating an enumerated condition (e.g. a renal or cystic condition, e.g., PKD) by the administration of a biologically or therapeutically effective amount of the combination product.

The crystal precipitation inhibitor composition may comprise any agent that inhibits the formation of crystals in physiological contexts, for example, the formation of calcium oxalate crystals, the formation of calcium phosphate crystals, and the formation of uric acid crystals. In one embodiment, the crystal precipitation inhibitor is a calcium chelator. In some embodiments, the crystal precipitation inhibitor composition is a buffering agent or pH-modulating agent that changes pH to inhibit crystal precipitation, for example, a pH-raising agent which inhibits uric acid crystal formation.

In a primary embodiment, the crystal precipitation-modulating composition is citrate. Citrate, as referred to herein, encompasses citric acid itself, or salts and esters of citric acid. For example, citrate may comprise a mono-, di- or tri-valent salt of citrate with sodium, potassium, magnesium, calcium, other cations, or mixtures of cations, or mixtures of citric acid with citrate salts. For example, citrate may comprise a mono-salt, for example a mono-sodium salt, for example, the sodium salt of STRUCTURE 4, or other salts wherein a different cation is used:

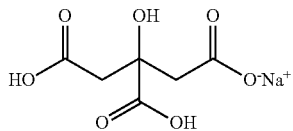

In one aspect, the scope of the invention encompasses a novel combination product comprising a ketonic composition and citrate, e.g. BHB or a BHB analog (such as a BHB precursor) in combination with citrate. In a related embodiment, the scope of the invention encompasses methods of supporting health, e.g. renal health, or treating an enumerated condition (e.g. a renal or cystic condition, e.g., PKD) by the administration of a biologically or therapeutically effective amount of the combination product comprising BHB or a BHB analog an citrate. Citrate may be administered as a salt of magnesium, potassium, calcium, sodium, or other forms. The use of citrate alone in the treatment of polycystic kidney disease in rats has been disclosed, for example, by Tanner and Tanner, Dietary Citrate Treatment of Polycystic Kidney Disease in Rats Nephron Physiol 200393:p 14-p 20 and in Tanner, Tanner, Potassium citrate/citric acid intake improves renal function in rats with polycystic kidney disease, JASN July 1998, 9 (7) 1242-1248. However, the combination of BHB or other ketones and citrate has not been disclosed.

In some embodiments, the crystal precipitation-modulating composition is a citrate analog, for example, a composition having structural similarity to citrate and retaining the crystal precipitation-modulating properties of citrate. Exemplary citrate analogs include derivatives of citric acid known in the art. Exemplary citrate analogs include esters of citric acid (e.g. monoester, diester, triester), amides of citric acid, 1,3 dioxal-4-ones, sidophores, peroxycitric acid, hydroxycitrate, and tricarballylic acid. Exemplary citrate analogs include compositions described in Milewska, 1988, Citric Acid, its natural and synthetic derivatives, Z Chem 28: 204-211.

In some embodiments, the crystal precipitation inhibitor is a composition that alkanizes urine, such as a carbonate or bicarbonate composition, such as magnesium carbonate or bicarbonate, calcium carbonate or bicarbonate, or sodium carbonate or bicarbonate. In some embodiments, the crystal precipitation-modulating composition is a compound that can decrease the level of uric acid in the urine and may be used to treat hyperuricemia. Such compounds will decrease the risk of formation or uric acid crystals. Three examples are allopurinol, oxypurinol and febuxostat, inhibitors of xanthine oxidase, that act on purine catabolism, reducing the production of uric acid. Another example is Lesinurad which inhibits the function of transporter proteins involved in renal uric acid reabsorption (uric acid transporter 1 [URAT1] and organic anion transporter 4 [OAT4]), and lowers serum uric acid levels. Another example is Rasburicase, a recombinant urate-oxidase enzyme, which converts uric acid to allantoin (an inactive and soluble metabolite of uric acid).

In various implementations, the therapeutic compositions of the invention comprise a combination of a ketonic composition, e.g., one or more of BHB, a BHB analog, and/or a GPR109A activator, in combination with one or more crystal precipitation-modulating compositions, for example, a combination of BHB and citrate, for example an admixture of the two in a capsule, tablet, powder, beverage, or edible item. By formulating the therapeutic compositions of the invention as combination products, the recipient may advantageously be administered a single agent with dual, synergistic therapeutic properties.

In an alternative implementation, the combination product is provided with the ketonic composition and crystal precipitation inhibitor as two separate dosage forms, optionally packaged in a single package. For example, two separate tablets, capsules, powders. e.g. a BHB capsule and a citrate capsule, may be provided with instructions to take them at the same time. By formulating the therapeutic compositions of the invention as individual entities, the recipient may benefit from the synergistic therapeutic properties but advantageously has the option to modify the individual doses according to specific needs.

It will be understood that citrate is a common additive to dietary supplements and other food items. For example, sodium citrate or potassium citrate are known additives used as flavoring agents, preservatives, and pH buffers. The quantity of citrate used for such purposes is therapeutically insignificant. The scope of the invention encompasses synergistic combination products comprising citrate wherein the quantity of citrate is biologically effective, i.e. sufficient to inhibit crystal precipitation in vivo, for example, crystal precipitation in the kidney. For example, when citrate is configured for oral administration, the biologically effective dosage may be in the range of 100 mg to 10 grams citrate per day. In various embodiments, the citrate dose is about or at least 10, 20, 30, 40, 50, 60, 70, 80, 90, 100, 120, 130, 140, 150, 160, 170, 180, 190, 200, 250, 300, 350, 400, 450, 500, 550, 600, 650, 700, 750, 800, 850, 900, 950 or 1,000 mg citrate or citrate salt per dose, per dosage form, or cumulative dosing per day. In an alternative method of assessing citrate dose, the dose may be in the range of 0.1 mmol-10 mmol citrate/100 g body weight per dosage, or per day, for example, a dosage of about or at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, 4.5, 5.0, 5.5, 6.0, 6.5, 7.0, 7.5, 8.0, 8.5, 9.0, 9.5, or 10 mmol citrate/100 g body weight per dose, or cumulative dose per day. In another method of dosage calculation, the citrate dosage is in the range of 0.1 to 10 mg citrate or citrate salt per $m^2$ body area per dosage or per day, for example at being about or at least 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5 or 10 mg per $m^2$ body area.

In some implementations, the biologically effective citrate is defined in terms of its abundance relative to the co-administered ketonic agent, e.g. BHB or a BHB analog. For example, in various embodiments, the ratio of citrate molecules, or mass of citrate, to BHB or BHB analog molecules (or mass) is in the range of 1:10 to 10:1. Exemplary ratios of citrate to BHB or BHB analog (by molecule or by mass) are in the range of 1:5, 1:4, 1:3, 1:2, 1:1, 2:1,3:1, 4:1 or 5:1.

In some implementations, the amount of citrate in the combination product is described in terms of the weight percentage of citrate in the combination product. In one embodiment, the weight percentage of citrate is calculated as proportional mass of citrate to the mass of citrate and the one or more ketonic compositions (e.g. the weight percentage of citrate with respect to active ingredients only). With respect to this measure, the weight percentage of citrate may be in the range of at least 5%, at least 10%, at least 15%, at least 20%, at least 25%, at least 30%, at least 35%, at least 40%, at least 45%, at least 50%, at least 55%, at least 60%, at least 70%, at least 80%, at least 90% or at least 95%. In one embodiment, the weight percentage of citrate is calculated as the proportional mass of citrate to the mass of the entire formulation, including citrate, ketonic compositions, and carriers and other inert ingredients (e.g. the weight percentage of citrate with respect to the entire product). With respect to this measure, the weight percentage of citrate may be in the range of at least 5%, at least 10%, at least 15%, at least 20%0%, at least 25%, at least 30%, at least 35%, at least 40%, at least 45%, at least 50%, at least 55%, at least 60%, at least 70%, at least 80%, at least 90% or at least 95%.

Bi-Functional Molecules. In one embodiment, the scope of the invention encompasses novel compositions, advantageously comprising a bi-functional molecule comprising one or more ketonic compositions, e.g. one or more of BHB, a BHB analog, or a GPR109A agonist, conjugated to one or more molecules of a crystal precipitation-modulating agent. In various embodiments, the dietary supplements and therapeutic compositions of the invention comprise such compositions. The use of such compositions advantageously provides a ketosis mimic and/or GPR109A agonist in combination with a crystal precipitation inhibitor in a single composition, at a desirable stoichiometric ratio. Additionally, the bi-functional molecules may be designed to be neutral or less acidic, thereby avoiding or reducing the need for salt formulation.

In one embodiment, the bi-functional molecule comprises a BHB-citrate ester, comprising one or more BHB molecules and/or one or more a BHB analog molecules conjugated to citrate. Exemplary BHB-citrate esters include STRUCTURE 5:

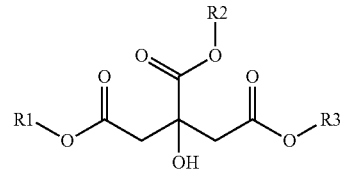

wherein R1, R2, or R3 may be hydrogen, alkyl, or another composition, and at least one of R1, R2, and R3 is ketonic composition. In one embodiment, R1, R2, or R3 may be hydrogen, alkyl, or another composition, and at least one of R1, R2, and R3 is BHB. In one embodiment, R1, R2, or R3 may be hydrogen, alkyl, or another composition, and at least one of R1, R2, and R3 is a BHB analog. In one embodiment, R1, R2, or R3 may be hydrogen, alkyl, or another composition, and at least one of R1, R2, and R3 is 1,3 butanediol. In one embodiment, R1, R2, or R3 may be hydrogen, alkyl, or another composition, and at least one of R1, R2, and R3 is a GPR109A activator.

Exemplary bi-functional molecules include Structure 6:

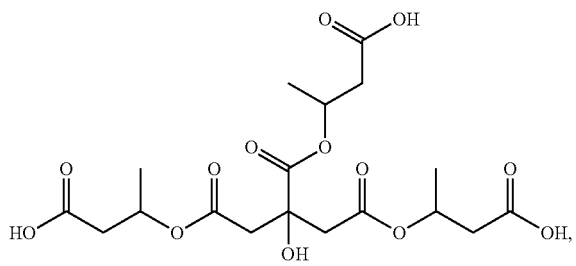 [SMILES: CC(CC(=O)O)OC(=O)CC(O)(CC(=O)OC(C)CC(=O)O)C(=O)OC(C)CC(=O)O]

Structure 7:

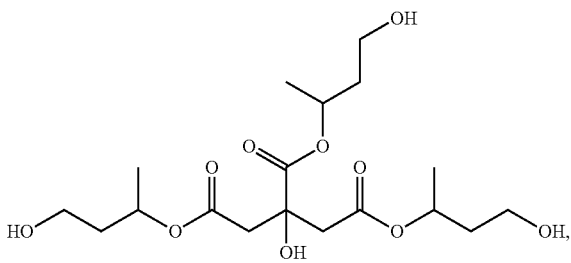 [SMILES: CC(CCO)OC(=O)CC(O)(CC(=O)OC(C)CCO)C(=O)OC(C)CCO]

Structure 8:

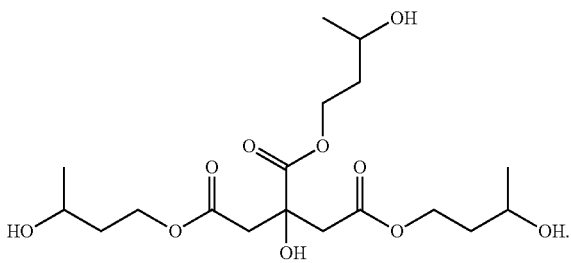 [SMILES: CC(O)CCOC(=O)CC(O)(CC(=O)OCCC(C)O)C(=O)OCCC(C)O]

Synthesis of Bi-Functional Molecules.

The bi-functional BHB-citrate esters and like composition of the invention may be synthesized according to known methods for the esterification of citrate and like molecules. For example Fischer-Speier esterification may be employed by refluxing citric acid with an excess of 1,3-butanediol in the presence of an acid catalyst such as sulfuric acid. Such a reaction is expected to yield a mixture of structures 7 and 8 as well as mixed esters with the 1,3-butanediol component esterified variously via the 1 and 3 positions in addition to other possible combinations. In all such cases, the in vivo hydrolysis of the bi-functional esters is expected to yield the functional components citrate and 1,3-butanediol. If more specific and pure bi-functional esters are desired, many commonly known chemical synthesis steps are available. For example, the hydroxyl group of citric acid could be protected by acetylation. e.g. using acetic anhydride, prior to carrying out the Fischer-Speier esterification described above. Similarly, precursors to 1,3-butanediol—in which either the 1-OH group or the 3-OH group is protected—could be used as starting material in the Fischer-Speier esterification.

Combination Product Comprising Lipotoxic Compositions.

Due to the metabolic inflexibility of epithelial cells in cysts, such as PKD cysts, for example, ADPKD cysts, in some implementations, the compositions and methods of the invention encompasses a combination product comprising a ketonic composition, e.g., one or more of BHB, a BHB analog, and/or a GPR109A activator, and a lipotoxic agent. The lipotoxic agent may comprise any fatty acid or other composition which create toxicity for cells that are dependent upon glucose for energy production and may be defective in beta-oxidation of fatty acids, i.e. having enhanced sensitivity to lipotoxicity from lipids that accumulate but which cannot be metabolized. Exemplary glucose dependent cells include cyst epithelial cells, including PKD cyst epithelial cells and liver cyst epithelial cells, and cancer cells.

In one embodiment, the lipotoxic composition is an MCT, as described above. Exemplary MCTs include triglycerides comprising six to 12-carbon chains, including caproic acid, caprylic acid, capric acid, and lauric acid.

Additionally, unsaturated fatty acids may act as lipotoxic agents for glucose-dependent cells. Exemplary unsaturated fat acids include monounsaturated and polyunsaturated fats such as α-Linolenic acid, Stearidonic acid, Linoleic acid, Linolelaidic acid, γ-Linolenic acid, Palmitoleic acid, Vaccenic acid, Oleic acid. Such unsaturated fatty acids may be administered alone or in mixtures as free fatty acids or their salts or as triglycerides. Alternatively, these unsaturated fatty acids may be administered in the form of natural fats and oils that are rich in these unsaturated fatty acids, for example including oils from flaxseed, walnuts, chia, hemp, and other vegetable oils.

The lipotoxic agents advantageously compositions that can be taken orally and which are used in various food products and supplements. In one embodiment, the lipotoxic agents are included in dietary supplements of the invention. The dosage of lipotoxic agents will be in the range of 0.5-100 g per day, for example about 1, 5, 10, 15, 20, 25, 30, 35, 40, 45, 50, 55, 60, 65, 70, 75, 80, or 90 g per day.

In certain embodiments, the combination product comprising a ketonic composition and a lipotoxic composition further includes a crystal precipitation-modulating agent (e.g. citrate). For example, the combination product may comprise BHB (or a BHB analog) in combination with citrate (or a citrate analog) in combination with one or more lipotoxic compositions, representing a tri-functional agent.

Formulations of the Ketonic Compositions and Combination Products.

It will be understood that the ketonic compositions and combination products containing such described herein may be formulated in various ways for effective and controlled delivery. It will be understood that the compositions may comprise the active agents described herein in combination with any number of ingredients that facilitate effective ingestion, administration, delivery, adsorption, distribution, and metabolism of the active agents. In various embodiments, the compositions described herein comprise dietary supplements, or therapeutic compositions (including therapeutic compositions formulated as dietary supplements). Further, all compositions described herein containing or comprising ketonic agents may be considered "medicaments." Furthermore, the act of manufacturing, including formulating, ketonic agents into dietary supplements, therapeutic compositions, or any ingested or otherwise administered compositions will be presumed to be performed under any specified processes therefor, and if no process is specified, then the act of manufacture, including formulation, will be assumed to be achieved by standard means known in the art, Thus recital of any described compositions wherein ketonic compositions are included, will be presumed to encompass an implied method of making such medicaments.

In various embodiments, the ketonic composition (e.g. BHB, BHB analog, and/or GPR109A activator) is formulated as a salt. Pharmaceutical salt formulations are known in the art and may impart higher solubility, stability, and bioavailability to the therapeutic molecules. Exemplary salts include salts of amino acids, alkali metals, alkaline earth metals, transition metals, for example: arginine salts, calcium salts, chromium salts, citrulline salts, cobalt salts, copper salts, creatine salts, glutamine salts, histidine salts, iron salts, isoleucine salts, leucine salts, lithium salts, lysine salts, magnesium salts, manganese salts, molybdenum salts, ornithine salts, potassium salts, selenium salts, sodium salts, and zinc salts.

In one primary implementation, the ketonic agents of the invention are formulated in a low-salt or zero-salt formulation, to avoid stressing the body, especially the kidneys, of the recipient. For example, a low-sodium and low-potassium and low-calcium formulation may comprise a formulation that would lead to an added sodium or potassium or calcium intake of no more than 500 mg/day each, preferably less.

The ketonic compositions of the invention may be formulated for efficient delivery by a selected route. The ketonic compositions of the invention may be formulated in combination with pharmaceutically acceptable excipients, carriers, diluents, release formulations and other drug delivery or drug targeting vehicles, as known in the art.

Advantageously, the ketonic compositions of the invention are amenable to efficient oral delivery and may be formulated therefor. Oral formulations may include any number of fillers, flavoring agents, coloring agents, sweeteners, and other compositions used in the art for oral delivery of agents. In one embodiment, the pharmaceutical composition is formulated for oral delivery in tablets or capsules. In one embodiment, the pharmaceutical composition is formulated as a powder to be mixed with liquid. In one embodiment, the ketonic composition is formulated as a liquid containing the therapeutic agent, i.e. solutions, such as water or other flavored drinks containing BHB or a BHB analog.

In alternative implementations, the ketonic compositions of the invention are formulated for administration via non-oral routes, including, for example, intravenous, intra-arterial, intraperitoneal, intrapulmonary, oral, inhalation, intra-vesicular, intramuscular, intra-tracheal, subcutaneous, intraocular, intrathecal, transmucosal, and transdermal delivery. In one embodiment, the ketonic compositions of the invention may be formulated for microbubble delivery for example, ultrasound meditated microbubble delivery, for site-specific delivery. In one embodiment, the ketonic compositions comprises nanoparticles containing or functionalized with the selected active agent of the ketonic composition, for delivery by nanoparticle-based delivery methods. In one embodiment, the ketonic composition comprises the selected therapeutic agent admixed with a polymeric material for timed release elution of the agent or to prevent premature digestion of the material in the digestive tract. In one embodiment, the ketonic composition comprises chemically conjugated magnetizable particles or use in magnetic-directed drug delivery methods, as known in the art. In one embodiment, the ketonic composition of the invention is coated onto an implant or drug eluting device.

In one embodiment, the therapeutic composition of the invention comprises a targeting moiety that facilitates delivery to a target cell type or organ, such as the kidneys, liver, cysts, or other sites. In one embodiment, the ketonic composition of the invention is conjugated to a polymeric immunoglobulin such as a polymeric IgM or IgA. Such agents may be efficiently targeted to renal cysts, for example, cysts present in the case of polycystic kidney disease.

Administration.

The various methods of the invention may encompass the administration of an agent to a subject. Administration, as used herein, may encompass the act of providing the agent to the subject or actually introducing the agent into the subject. Administration as used herein will encompass self-administration. For example, in a primary implementation of the methods of the invention, dietary supplements are ingested by a subject. Such ingestion will be considered administration. i.e., self-administration of the enumerated composition. Administration may also comprise provision of a selected composition to the subject, for example, providing food or liquids that contain the composition to an animal.

Dietary Supplements.

In a primary implementation of the methods of the invention, the ketonic composition is formulated and administered as a dietary supplement. A dietary supplement is a composition that is administered orally, for example, in food or drink, with food or drink, or which otherwise supplements the regular intake of food. From a regulatory standpoint, a dietary supplement is generally a composition that can be purchased and used without a prescription. For example, in the United States, per the Food and Drug Administration and The Dietary Supplement Health and Education Act of 1994, a dietary supplement is "a product intended to supplement the diet that bears or contains one or more of the following dietary ingredients: a vitamin, a mineral, an herb or other botanical, an amino acid, a dietary substance for use by man to supplement the diet by increasing the total dietary intake, or a concentrate, metabolite, constituent, extract, or combination of any ingredient just described."

The dietary supplements of the invention may encompass any formulation for oral delivery. In a primary implementation, the ketonic compositions of the invention are ingested in liquids, for example, being formulated in any number of beverage formats, including infused water, sports drinks, energy drinks, teas, fruit juices, or meal replacement beverages. In one embodiment, the ketonic compositions of the invention are formulated as a powder which may be dissolved in water, or other drinks such as fruit juice, coffee, or tea. In some embodiments, the powder is packaged in individual packets or vials at a measured dose. In some embodiments, the powder is packaged with a scoop which measures the correct dose for mixing with liquid and instructions for doing so at a specified frequency.

In an alternative dosage form, the dietary supplement of the invention is formulated as a capsule, tablet, or chewable tablet. In some implementations, the dietary supplements of the invention are ingested as a component of an edible item, for example, being incorporated into gummies, cookies, snack bars, meal replacement bars and other bars, cereals, biscuits, crackers, confectionery items, and probiotic formulations including yogurt, and other food items. In some cases the dietary supplements of the invention are formulated as products for non-human animals, such as chow, feed, treats or snacks, or supplemented pet food.

In the case of combination products comprising a ketonic composition in combination with a secondary agent (e.g. a crystal precipitation inhibitor such as citrate or a lipotoxic agent such as unsaturated fatty acids), the dietary supplements are preferably formulated as a single product containing both the ketonic composition (e.g. BHB or BHB analog) and the secondary agent so that only a single product is required to be digested. However, it will be understood the scope of the invention includes separate formulations and dosage forms of the ketonic composition and secondary agents, to be ingested separately.

Part 2: Methods of Use

The scope of the invention encompasses numerous methods directed to the use of ketonic compositions for the maintenance of health, prevention of disease, and in therapeutic applications. In one aspect, the scope of the invention encompasses methods of using dietary supplements comprising ketonic compositions for supporting health. In another aspect, the scope of the invention encompasses the use of ketonic compositions in therapeutic methods for the prevention and treatment of various diseases and pathological conditions.

The methods disclosed herein will be directed to the use of ketonic compositions by, and administration of ketonic compositions to, subjects. The subject may be a human subject, for example, in some contexts, a patient. The subject may comprise a non-human animal of any species, including test animals, veterinary subjects, pets, and livestock, for example, any of mice, rats, dogs, cats, sheep, goats, cows, pigs, horses, camels, non-human primates, or other animals. For example, polycystic kidney disease is prevalent in dogs and cats.

In certain embodiments, the subject of the method will be a subject in need of treatment for a selected condition. For example, the subject may be a subject suffering from a condition, may be symptomatic of a selected condition, or may be at risk of a selected condition.

The methods of the invention encompass the ingestion and administration of ketonic agents in a biologically or therapeutically effective amount. In one measure, a biologically or therapeutically effective amount is an amount of ketonic agent ingested as dietary supplement or administered therapeutically that is sufficient to induce a ketonic response. Such a response may be indicated by assaying the elevated blood concentration of a ketone body such as BHB. A response could also be measured by assaying a change in the blood levels of fatty acids that can be used as an indicator of the anti-lipolytic consequences of GPR109a activation. In one measure, a ketonic response is the elevation of ketones in the blood or other compartment of the subject, for example, any significant elevation compared to subjects not experiencing ketosis. In one measure, a ketonic response is the increase in GPR109A activation in selected target cells of the subject, for example, any significant increase in GPR109A activity compared to subjects not ingesting or administered a ketonic agent. In one measure, a ketonic response is the attainment of a specific physiological outcome or state, for example, the mean or median dosage required to attain the selected outcome in a significant portion of representative subjects, compared to subjects not ingesting or administered the ketonic agent. Selected outcomes may encompass any relevant outcome, such as reduced symptoms of a selected condition, for example, reduced size or abundance of cysts in the case of cystic disease, improved organ or cellular function, and other physiological or health measures.

The dietary supplements and therapeutic ketonic agents of the invention are ingested or administered in a dose, being an amount of ketonic composition ingested or otherwise received at a time or over a specified timeframe (e.g. a daily dose). Doses may be referred to as approximate amounts, for example, being "about X mg." "About," as used herein means, in various embodiments, within plus-or-minus 10%, plus-or-minus 5%, or plus-or-minus 1% of the enumerated value.

In various embodiments, the ingested or administered ketonic composition is BHB, or a BHB analog, e.g. a BHB precursor, configured for oral administration, wherein the administration is oral, and the biologically effective or therapeutically effective dosage is in the range of 0.1 to 50 grams BHB per day, e.g., for humans. For example, daily doses of about or at least 100 mg, about or at least 250 mg, about or at least 500 mg, about or at least 1 gram, about or at least 2 grams, about or at least 3 grams, about or at least 4 grams, about or at least 5 grams, about or at least 6 grams, about or at least 7 grams, about or at least 8 grams, about or at least 9 grams, about or at least 10 grams, about or at least 12 grams, about or at least 15 grams, or about or at least 20 grams may be ingested or administered. In some embodiments, the dosage of BHB, BHB analog, including BHB precursors, is in the range of 10-200 mg/Kg body weight, for example, 10, 25, 50, 75, 100, 125, 150, 175, or 200 mg/Kg. For non-human animal subjects, such as animal models or pets, the exemplary dosages above may be adjusted based on the difference in body weight or body surface area. In one embodiment, the non-human is a small animal (e.g. rodent, dog, or cat) and the biologically or therapeutically effective amount of BHB or BHB analog is in the range of 10-150 mg/Kg, in various embodiments, for example, being about 10, 20, 30, 40, 50, 60, 70, 80, 85, 90, 95, 100, 120, 150 mg/Kg.

In an alternative measure, the biologically effective or therapeutically effective amount of BHB or BHB analog is determined as the amount necessary to raise blood ketone levels (e.g., BHB levels) to a selected threshold indicative of ketosis, for example, a dose sufficient to attain a blood concentration of BHB at least 0.250 to 5 mMol BHB per liter of blood, for example, about or at least 0.250, about or at least 0.500, about or at least 0.750, about or at least 1.0, about or at least 2.0, about or at least 3.0 mMol BHB per liter of blood.

In the case of GPR1009A activators, the biologically or therapeutically effective dose will be determined by the potency, ADMET, and delivery route of the selected GPR109A activator. This class of compositions includes potent small molecules that act in the picomolar to nanomolar range, as well as ketones and other orally available compositions (e.g. niacin) that require higher concentrations to induce GPR109A activation in selected target cells (e.g. cyst epithelial cells). Accordingly, the biologically or therapeutically effective dose of GPR109A activator may be determined by one of skill in the art based on the properties of the agent and the desired therapeutic outcome.

In the case of a combination product comprising a crystal precipitation inhibitor, e.g. citrate, a biologically or therapeutically effective amount is an amount of crystal precipitation inhibitor ingested or administered that is sufficient to inhibit crystal formation in vivo, e.g. uric acid crystal formation or calcium crystal formation, or sufficient to induce conditions that inhibit crystal formation, such as increased urinary concentration of citrate to antagonize calcium crystal precipitation, or increased urinary pH to antagonize uric acid crystal precipitation, or reduced blood or urine levels of uric acid to antagonize uric acid crystal precipitation.

In various embodiments, the selected crystal precipitation inhibitor, for example, citrate, is configured for oral administration, the administration is oral, and, for example in humans, the biologically or therapeutically effective dose ingested or administered may be in the range of 100 mg to 15 grams, for example, at least or about 100 mg, at least or about 200 mg, at least or about 300 mg, at least or about 500 mg, at least or about 1 gram, at least or about 2 grams, at least or about 3 grams, at least or about 4 grams, at least or about 5 grams, at least or about 6 grams, at least or about 7 grams, at least or about 8 grams, at least or about 9, grams, or at least or about 10 grams. In some embodiments, the dosage of citrate or citrate analog is in the range of 5-100 mg/Kg body weight, for example, in various embodiments, being 5, 10, 20, 25, 30, 40, 50, 55, 65, 70, 75, 80, 85 90, or 100 mg/Kg. For non-human animal subjects, such as animal models or pets, the exemplary dosages above may be adjusted based on the difference in body weight or body surface area. In one embodiment, the non-human is a small animal (e.g. rodent, dog, or cat) and the biologically or therapeutically effective amount of citrate or citrate analog is in the range of 10-100, for example, 25-75 mg/Kg, in various embodiments, for example, being about 10, 20, 30, 40, 45, 50, 55, 60, 65, 70, 80, 90 or 100 mg/Kg.

The dosage of the crystal precipitation inhibitor, e.g., citrate, in the dietary supplement may be determined by alternate measures. For example, in one embodiment, the crystal precipitation inhibitor, such as citrate, is ingested or administered at a dosage of between 0.1 mmol-10 mmol/100 g body weight per day, for example, at least 0.5, at least 1, at least 2, at least 5, at least 7.5 or at least 10 mmol/100 g body weight per day. In another embodiment, the crystal precipitation inhibitor, such as citrate, is ingested or administered at a dosage of between 0.5 to 10 mg/citrate or citrate salt per $m^2$ body area per day, for example at least 1, at least 2, at least 3, at least 4, or at least 5 mg per $m^2$ body area, per day.

Doses may be ingested or administered according to a selected health or treatment regimen. In some embodiments, doses are ingested or administered for a selected period of time, e.g. a period of days, weeks, or months. In some implementations, especially in preventative methods, chronic, long-term ingestion or administration is contemplated for maintaining beneficial, therapeutic, or preventative effects. In a primary embodiment, the administration is daily with one or more dosages ingested or administered per day.

Multiple such dosages may be administered during the day, to arrive a cumulative dosage near, at, or above the biologically effective or therapeutically effective daily dosage, for example, two, three, four, or more doses per day. Dosage forms (e.g. capsules, packets of dissolvable powder for drinks, scoops for measuring such powder, etc.) may be configured for fractions of the daily dose. In some implementations, two or more dosages are delivered per day, for example, a morning and an evening dose, a dosage administered before or after each meal, a dosage delivered every four hours, six hours, twelve hours, or at other selected time intervals. Advantageously, a low dosage of BHB, administered multiple times per day, may be more palatable than a full daily dosage, wherein the unpleasant taste of BHB is an issue. Likewise, by administering low dosages of citrate over multiple daily administrations, gastrointestinal issues associated with long term citrate consumption can be alleviated. In alternative embodiments, the dietary supplement is consumed at less than daily frequency, for example, once a week, twice a week, three times a week, etc.

Exemplary Dietary Supplements and Therapeutic Compositions.

The methods of the invention will encompass the administration or ingestion of ketonic compositions in a dietary supplement or a therapeutic composition. The dietary supplement or therapeutic composition may comprise any of the ketonic compositions, combination products, and formulations, as disclosed in the previous sections, In various embodiments, the dietary supplement or a therapeutic composition comprises an exemplary formulation as forth below.

The dietary supplement or a therapeutic composition will comprise a ketonic composition. The ketonic composition may comprise one or more of BHB, a BHB analog, a GPR109A agonist, or a combination of the foregoing. The formulations may comprise a combination of two or more different ketonic compositions. In some embodiments, ketonic composition comprises a BHB analog, wherein the BHB analog may comprises an ester of BHB, a BHB precursor, 1,3-butanediol, or a bi-functional composition comprising one or more molecules of BHB, a BHB analog, and/or a GPR109A agonist conjugated to one or more molecules of citrate. In some embodiments, the bi-functional molecule is Structure 5. Structure 6, Structure 7, or Structure 8. In some embodiments, the composition comprises L-BHB, for example, at least 10% L-BHB, about 50% L-BHB, or substantially pure L-BHB. In some embodiments, the ketonic composition comprises a GPR109A agonist, wherein the GPR109A agonist comprises a composition selected from the group consisting of niacin, a niacin analog, clotrimazole, GSK256073, MK-1903, monomethylfumarate acipimox, acifran, 3-pyridine-acetic acid, 5-methylnicotinic acid, pyridazine-4-carboxylic acid pyrazine-2-carboxylic acid, LUF6281, LUF6283, a pyrazolyl propionyl cyclohexenamide, an acyl hydroxypyrazole, and SCH900271.

The dietary supplement or therapeutic composition will comprise a ketonic composition in a biologically or therapeutically effective amount. In some embodiments, the biologically or therapeutically effective amount is an amount sufficient to attain blood ketone levels at a level indicative of ketosis, for example, a dose sufficient to attain a blood concentration of BHB at least 0.250 to 5 mMol BHB per liter of blood, for example, about or at least 0.250, about or at least 0.500, about or at least 0.750, about or at least 1.0 mMol BHB per liter. In various embodiments, the ketonic agent comprises BHB and the biologically or therapeutically effective amount is an amount in the range of 0.1 to 50 grams BHB, for example, 0.1 to 50 grams BHB per day. In various embodiments the biologically or therapeutically effective amount is about or at least 100 mg, about or at least 250 mg, about or at least 500 mg, about or at least 1 gram, about or at least 2 grams, about or at least 5 grams, or, about or at least 10 grams.

In various embodiments the dietary supplement or therapeutic composition will comprise a ketonic composition in combination with a biologically or therapeutically effective amount of a crystal precipitation inhibitor. In one embodiment, the biologically or therapeutically effective amount of a crystal precipitation inhibitor is an amount sufficient to inhibit in vivo crystal precipitation, for example, sufficient to inhibit the formation of calcium oxalate crystals, the formation of calcium phosphate crystals, and/or the formation of uric acid crystals. In some embodiments, the crystal precipitation inhibitor is a calcium chelator. In some embodiments, the crystal precipitation inhibitor is a buffering agent or pH-modulating or alkanizing agent.

In various embodiments the crystal precipitation inhibitor is selected from the group consisting of citrate, hydroxycitrate, esters of citric acid (e.g. monoester, diester, triester), amides of citric acid, 1,3 dioxal-4-ones, sidophores, peroxycitric acid, hydroxycitrate, and tricarballylic acid, a composition that alkanizes urine, a carbonate or bicarbonate, magnesium carbonate or bicarbonate, calcium carbonate or bicarbonate, or sodium carbonate or bicarbonate, allopurinol, oxypurinol and febuxostat, inhibitors of xanthine oxidase, Lesinurad. Rasburicase, and a calcium chelator. In one embodiment the crystal precipitation inhibitor is citrate. In various embodiments, the biologically effective biologically or therapeutically effective amount is at least 100 mg citrate, for example, 200 mg citrate per day, at least 500 mg citrate, for example, 500 mg citrate per day, citrate at a weight percentage in the dietary supplement or therapeutic composition of at least 5%, at least 10%, at least 20%, at least 30%, at least 40%, or at least 50%.

In various embodiments the dietary supplement or therapeutic composition will comprise a ketonic composition in combination with a biologically or therapeutically effective amount of a lipotoxic agent. In one embodiment, the biologically or therapeutically effective amount of a lipotoxic agent is an amount sufficient to cause lipotoxic effects in glucose-dependent cells, e.g., PKD cyst epithelial cells, in various embodiments, biologically or therapeutically effective amount of a lipotoxic agent is in the range of 0.5-100 g per day, for example about 1, 5, 10, 15, 20, 25, 30, 35, 40, 45, 50, 55, 60, 65, 70, 75, 80, or 90 g per day. In one embodiment, the lipotoxic agent comprises MCT. In one embodiment, the lipotoxic agent comprises fatty acids.

In one embodiment, the dietary supplement or therapeutic composition comprises a ketonic composition in combination with both a biologically or therapeutically effective amount of a crystal precipitation inhibitor and a biologically or therapeutically effective amount of a lipotoxic agent.

The dietary supplements of the invention are by definition formulated for oral delivery. In various embodiments, the therapeutic compositions may also be formulated for oral delivery. In one embodiment, the therapeutic composition is formulated for oral delivery as a dietary supplement. In various embodiments the dietary supplement or therapeutic composition is formulated as a capsule, a chewable tablet, a tablet, a dissolvable powder, a beverage, or a food item.

In the case of dietary supplements or therapeutic compositions comprising a ketonic composition in combination with a secondary agent (e.g. a crystal precipitation inhibitor such as citrate or a lipotoxic agent such as unsaturated fat acids), the dietary supplement or therapeutic composition may be formulated as a single product containing both the ketonic composition (e.g. BHB or BHB analog) and the secondary agent so that only a single product is required to be ingested or administered. In another embodiment, the ketonic composition and the secondary agent(s) (e.g. a crystal precipitation inhibitor such as citrate or a lipotoxic agent) are provided together in separate dosage forms, for example, capsules or chewable tablets, for example, to be ingested at the same time.

Methods of Supporting Health by the Use of Dietary Supplements.

In one aspect, the scope of the invention encompasses novel methods of promoting health and wellness by the use of dietary supplements comprising ketonic compositions. In various embodiments, the function of the compositions and methods of the invention will be described as "supporting health," for example, "supporting renal health." As used herein, supporting a enumerated type of health will encompass any activity that maintains, enhances, improves, or promotes relevant organ or cellular function, for example, renal function in the case of supporting renal health. In various embodiments, the support of health is achieved by ameliorating the risk, progression, and/or severity of a condition. Ameliorating the risk, progression, and/or severity of a condition may encompass any number of physiological, health, or medical processes, such as treating or preventing the condition in any way, reducing, reversing, or curing symptoms, pathologies, or pathological processes of the condition, slowing or halting the progression of the condition, or any other therapeutic or beneficial effect.

Methods of Treatment.

Certain methods of the invention encompass the prevention or treatment of a selected condition. As used herein, treatment will encompass any number of therapeutic effects and outcomes with respect to a selected condition, including, for example: a reduction in the severity of symptoms of the condition; the inhibition of pathological processes underlying the condition; the reversal of pathological events or processes of the condition; halting or slowing the progression of the condition; or a reduction in morbidity and/or mortality associated with the condition. Treatment, as used herein, will further encompass prevention of an enumerated condition. As used herein, prevention will encompass any number of actions with respect to a selected condition, for example: preventing the onset of the condition; reducing the probability of the condition occurring; halting the further progression of the condition, ameliorating underlying physiological parameters that promote the condition, or any other preventative action. As used herein, treatment will further encompass enhancements of target cell or organ function, such as quantitatively or qualitatively improved function, for example, in certain implementations, improved function, restoring normal function, or maintaining function.

Methods of Supporting Renal Health and Treating Renal Conditions.

In a primary aspect, the scope of the invention encompasses the use of ketonic compositions in dietary supplements and therapeutic compositions to address various aspects of renal health and renal conditions.

In one implementation, the scope of the invention encompasses a dietary supplement comprising a ketonic composition for use in a method of supporting renal health in a subject. In a related embodiment, the scope of the invention encompasses the use of a ketonic composition in a method of making a medicament for the support of renal health. In a related implementation, the scope of the invention encompasses a method of supporting renal health in a subject by the administration to the subject (for example, including self-administration, i.e. ingestion) of a biologically effective amount of a dietary supplement comprising a ketonic composition. In various embodiments, the dietary supplement comprises a ketonic composition in combination with a crystal precipitation inhibitor and/or a lipotoxic agent. In one embodiment, supporting renal health means maintaining or enhancing one or more measures of renal function. For example, renal function may be assessed by glomerular filtration rate, creatine clearance rate, urine output, proteinuria, or other measures of renal function known in the art. In one embodiment, supporting renal health in a subject is achieved by ameliorating the subject's risk, progression, and/or severity of one or more renal conditions.

In various embodiments, the scope of the invention further encompasses the use of therapeutic compositions comprising ketonic compositions for the treatment of renal conditions. In one embodiment, the scope of the invention encompasses a ketonic composition for use in a method of treating a renal condition. In a related embodiment, the scope of the invention encompasses the use of a ketonic composition in a method of making a medicament for the treatment of a renal condition. In one embodiment, the scope of the invention encompasses a method of treating a renal condition in a subject in need of treatment therefor by administering to the subject a therapeutically effective amount of a ketonic composition. The ketonic composition may be delivered or provided in a therapeutic composition, for example, a formulation comprising other components and/or active ingredients. In some embodiments, the dietary supplement comprises a ketonic composition in combination with a crystal precipitation inhibitor and/or a lipotoxic agent. In some embodiments, the treatment is a preventative treatment.

In the practice of the foregoing methods, the subject to which the dietary supplement or therapeutic composition is administered may be a subject in need of renal health support, for example, a subject having or at risk of a renal condition. A renal condition, as used herein, may encompass any pathological process, pathological state, disease, or dysfunction of the kidney. In various embodiments, for example, the subject is a human, a cat, or a dog.

In various embodiments, the renal condition is a cystic condition. In one embodiment, the cystic condition is PKD. In various embodiments, supporting renal health and/or treatment of a cystic conditions encompasses preventing or ameliorating any pathological effects of renal cysts, reducing or preventing the formation of renal cysts, reducing the number and/or size of renal cysts, slowing the growth rate of renal cysts, or eliminating renal cysts. In one embodiment, the cystic condition is ADPKD. In one embodiment, the polycystic kidney disease is autosomal recessive polycystic kidney disease (ARPKD). In various embodiments, the subject to which the dietary supplement or therapeutic composition is administered is a subject having PKD or at risk of PKD. In some embodiments, the subject at risk of PKD is a subject carrying a mutation in any of PKD1, PKD2, PKD3, or other genes wherein mutations increase the risk of PKD. In some embodiments, the subject at risk of PKD is a subject with health or demographic factors associated with PKD risk. In some embodiments, the subject is a human. In some embodiments, the subject is a dog or cat.

In other embodiments, the renal cystic condition is a condition selected from the group consisting of renal cysts as found in tuberous sclerosis complex, medullary cystic kidney disease, Acquired Cystic Kidney Disease, including acquired simple renal cysts, cystic renal cell carcinoma, and cystic nephroma.

In one embodiment, the renal condition is acute kidney injury (AKI). AKI encompasses kidney dysfunction or failure, and may be caused by many factors or causative agents. AKI manifests as damage to kidneys and impaired kidney functions, including progression along the RIFLE staging criteria known in the art, encompassing risk, injury, failure, loss, and end-stage renal disease. In various embodiments, the subject to which the dietary supplement or therapeutic composition is administered is a subject having or at risk of AKI. In various embodiments, a subject at risk of AKI is a subject having systemic disease, trauma, sepsis, renal artery stenosis, renal vein thrombosis, urinary tract obstruction, glomerulonephritis, acute tubular necrosis, acute interstitial nephritis, or liver cirrhosis. In various embodiments, a subject at risk of AKI is a subject having reduced blood flow to kidneys, such as by cardiac dysfunction or failure, surgery, trauma or ischemia. In various embodiments, a subject at risk of having AKI is a subject likely to be exposed to or being exposed to harmful levels of nephrotoxins such as mercury or platinum compounds, radiological contrast agents, and antibiotics. In one embodiment, the subject at risk of AKI is a subject likely to have or scheduled to have surgery, in one embodiment, cardiac surgery. In various embodiments, dietary supplement and/or therapeutic composition is administered as a pre-treatment prior to surgery and/or post-treatment after surgery in order reduce the risk or severity of AKI and to reduce the risk of developing complications therefrom, including chronic kidney disease.

In various embodiments, the renal condition is chronic kidney disease (CKD), encompassing any gradual loss or long-term impairment of kidney function. In various embodiments, the subject to which the dietary supplement or therapeutic composition is administered is a subject having or at risk of CKD. A subject at risk of CKD may be a subject having any known risk factor of CKD including, Type I or Type II diabetes mellitus, prior occurrence of acute kidney injury, glomerulomephritis, high blood pressure, or family history of CKD.

In various embodiments, the renal condition is a condition selected from the group consisting of: diabetic nephropathy, nephronophthisis, Meckel-Gruber syndrome, Bardet-Biedl syndrome, Joubert syndrome, medullary sponge kidney, multicystic dysplastic kidney, Dent's disease, Glomerulocystic kidney disease, Von Hippel-Lindau Syndrome, and mixed epithelial and stromal tumor of the kidney.

Methods of Supporting Health and Treating Reperfusion Injury.

In another aspect, the methods of the invention are directed to various conditions described as ischemic reperfusion injuries (IRI), sometimes referred to as reoxygenation injury. This class of pathologies is associated with the loss of blood flow in the affected organ, structure, or area. The hypoxia and loss of nutrients in the affected area promotes conditions wherein the subsequent restoration of circulation results in inflammation and damage caused by severe oxidative stress. The loss of circulation may be the result of trauma, injury, ischemic events, cardiac failure, or other causes. Surgery is also a causative agent of IRI, especially cardiac surgery, wherein reduced blood flow during the procedure facilitates IRI upon restoration of normal blood flow. IRI may affect any number of tissues, including the arteries and veins, brain, heart, liver, lungs, kidneys, skeletal muscle, and digestive tract.

In one implementation, the scope of the invention encompasses a dietary supplement comprising a ketonic composition for use in a method of supporting health with regards to ischemic reperfusion injury. In a related embodiment, the scope of the invention encompasses the use of a ketonic composition in a method of making a medicament for the support of health with regards to ischemic reperfusion injury. In a related implementation, the scope of the invention encompasses a method of supporting health with regards to ischemic reperfusion injury in a subject by the administration to the subject (for example, including self-administration, i.e. ingestion) of a biologically effective amount of a dietary supplement comprising a ketonic composition. In various embodiments, the dietary supplement may comprises a ketonic agent in combination with a crystal precipitation inhibitor. In one embodiment, supporting health with respect to ischemic reperfusion injury means maintaining or enhancing one or more measures of organ function, for example, function of the brain, heart, liver, lungs, kidneys, skeletal muscle, or digestive tract. In one embodiment, supporting health with respect to ischemic reperfusion injury in a subject is achieved by ameliorating the subject's risk, progression, and/or severity of one or more ischemic reperfusion injury conditions.

In another aspect, the scope of the invention encompasses the use of therapeutic compositions comprising ketonic compositions for the treatment of ischemic reperfusion injury conditions. In one embodiment, the scope of the invention encompasses a ketonic composition for use in a method of treating an ischemic reperfusion injury condition. In a related embodiment, the scope of the invention encompasses the use of a ketonic composition in a method of making a medicament for the treatment of ischemic reperfusion injury. In one embodiment, the scope of the invention encompasses a method of treating a ischemic reperfusion injury condition in a subject in need of treatment therefor by administering to the subject a therapeutically effective amount of a ketonic composition. The ketonic composition may be delivered or provided in a therapeutic composition, for example, a formulation comprising other components and/or active ingredients. In some embodiments, the therapeutic composition comprises a ketonic composition in combination with a crystal precipitation inhibitor. In some embodiments, the treatment is a preventative treatment.

In the foregoing methods of the invention, the subject to which the dietary supplement or therapeutic composition comprising a ketonic composition is administered is a subject in need of treatment for one or more ischemic reperfusion injuries, in some embodiments being a subject that has experienced, or is at risk of the one or more ischemic reperfusion injuries. In one embodiment, the subject at risk of ischemic reperfusion injury is a subject likely or scheduled to undergo surgery. In one embodiment, the dietary supplement or therapeutic composition is administered as a pre-treatment prior to surgery.

Methods of Supporting Neurological Health and Treating Neurodegenerative Conditions.

In various implementation, the methods of the invention are directed to maintaining or improving some aspect of neurological health, and to addressing neurological conditions, including conditions of the brain, central nervous system, and peripheral nervous system.

In one implementation, the scope of the invention encompasses a dietary supplement comprising a ketonic composition for use in a method of supporting neurological health. In a related implementation, the scope of the invention encompasses a method of supporting neurological health in a subject by the administration to the subject (for example, including self-administration, i.e. ingestion) of a therapeutically effective amount of a dietary supplement comprising a ketonic composition. In one embodiment, supporting neurological health means maintaining or enhancing one or more measures of neurological function, for example, cognitive function or motor function. In one embodiment, supporting neurological health in a subject is achieved by ameliorating the subject's risk, progression, and/or severity of one or more neurological conditions.

In another implementation, the scope of the invention encompasses therapeutic compositions comprising a ketonic composition for use in a method of treating a neurological condition. In a related embodiment, the scope of the invention encompasses the use of a ketonic composition in a method of making a medicament for treatment of a neurological condition. In a related embodiment, the scope of the invention encompasses a method of treating a neurological condition in a subject in need of treatment therefor, comprising administering to the subject a therapeutically effective amount of a therapeutic composition comprising a ketonic composition. In some embodiments, the therapeutic composition further comprises a crystal precipitation inhibitor and/or a lipotoxic agent. In some embodiments, the treatment is a preventative treatment.

In the foregoing methods, the subject to which the dietary supplement or therapeutic composition is administered may be a subject in need of treatment for one or more neurological conditions. A neurological condition, as used herein, may encompass any pathological process, pathological state, disease, or dysfunction of the central or peripheral nervous system, especially conditions that affect the brain, for example, a neurodegenerative disease. In various embodiments, the subject at risk of a neurological condition is has, or is at risk of the one or more neurological conditions. In one embodiment, the neurological condition is a neurodegenerative condition. In various embodiments, the neurological condition is selected from the group consisting of Alzheimer's disease, Parkinson's disease, multiple sclerosis, amyotrophic lateral sclerosis, Huntington's disease, epilepsy, chronic traumatic encephalopathy, age-related neurodegeneration, frontotemporal dementia, and retinitis pigmentosa.

Methods of Supporting Cilial Health and Treating Ciliopathies.

In some embodiments, the methods of the invention are directed to health aspects and conditions associated with the cilia. Cilia are a component of almost all vertebrate cells. Ciliopathies encompass a large group of disorders associated with cilial dysfunction, typically driven by genetic mutations encoding defective proteins which result in either abnormal formation of cilia or which disrupt their normal function. Ciliopathies include a wide array of conditions across various organs and systems of the body.

In one implementation, the scope of the invention encompasses a dietary supplement comprising a ketonic composition for use in a method of supporting cilial health. In a related embodiment, the scope of the invention encompasses the use of a ketonic composition in a method of making a medicament for the support of cilial health. In a related implementation, the scope of the invention encompasses a method of supporting cilial health in a subject by the administration to the subject (for example, including self-administration, i.e. ingestion) of a biologically effective amount of a dietary supplement comprising a ketonic composition. In one embodiment, supporting cilial health means maintaining or enhancing one or more measures of cilial function. In one embodiment, supporting cilial health in a subject is achieved by ameliorating the subject's risk, progression, and/or severity of one or more ciliopathies.

In another implementation, the scope of the invention encompasses a therapeutic compositions comprising a ketonic composition for use in a method of treating a ciliopathy. In a related embodiment, the scope of the invention encompasses the use of a ketonic composition in a method of making a medicament for the treatment of a ciliopathy. In a related embodiment, the scope of the invention encompasses a method of treating a ciliopathy in a subject in need of treatment therefor, comprising administering to the subject a therapeutically effective amount of a therapeutic composition comprising a ketonic composition. In some embodiments, the therapeutic composition further comprises a crystal precipitation inhibitor and/or a lipotoxic agent. In some embodiments, the treatment is a preventative treatment to a subject at risk of a ciliopathy.

In the foregoing methods, the subject to which the dietary supplement or therapeutic composition is administered may be a subject in need of treatment for one or more ciliopathies, in some embodiments being a subject that has, or is at risk of the one or more ciliopathies. In various embodiments, the ciliopathy is selected from the group consisting of polycystic kidney disease, polycystic liver disease, retinitis pigmentosa, congenital fibrocystic diseases of the liver, diabetes, obesity, skeletal dysplasia's, Ahlstrom syndrome, Bardet-Biedl syndrome, Joubert syndrome, nephronophthisis, orofaciodigital syndrome 1, Senior-Loken syndrome, primary ciliary dyskinesia, Jeune asphyxiating thoracic dysplasia, Marden-Walker syndrome, situs inversus or isomerism, retinal degeneration, agenesis of the corpus callosum, anencephaly, cerebellar vermis hypoplasia. Dandy-Walker malformation, diabetes, Ellis-van Creveld syndrome, exencephaly, eye movement abnormalities, hypoplasia of the corpus callosum, hypotonia, sterility, Jeune asphyxiating thoracic dystrophy, Juvenile myoclonic epilepsy, Marden-Walker syndrome, Meckel-Gruber syndrome, sensorineural deafness, and spina bifida.

Other Uses of Dietary Supplements.

In various embodiments, the dietary supplements and therapeutic compositions comprising ketonic agents may be utilized in methods of preventing or treating conditions such as cancer, a cystic condition of the liver, a pulmonary disease, autoimmune disease, a condition of the digestive tract, epilepsy, or infection.

In one embodiment, the dietary supplements and therapeutic compositions of the invention are used in the treatment of viral infection. It has been shown in the art that ketosis may increase the body's ability to fight viral infections, for example, as described in Goldberg et al., Ketogenic diet activates protective γδ T cell responses against influenza virus infection. *Science Immunology*, 2019; 4 (41): eaav2026. In one embodiment, the scope of the invention encompasses a dietary supplement comprising a ketonic composition for use in a method of preventing or treating viral infection. In one embodiment, the scope of the invention encompasses a method of treating a viral infection, for example, preventing viral infection, in a subject by the administration to the subject of a therapeutically effective amount of a therapeutic composition comprising a ketonic composition. The viral infection may an infection caused by any pathogenic virus, for example influenza viruses, coronaviruses such as COVID19, HIV, noroviruses, respiratory syncvtial viruses, herpes viruses, and papillomaviruses.

EXAMPLES

Example 1. Dietary Ketosis and Exogenous BHB Ameliorate Renal Cyst Growth in Polycystic Kidney Disease A key signaling molecule activated in ADPKD is the kinase mammalian target of rapamycin (mTOR) that regulates many cellular behaviors including proliferation, cell growth, and energy metabolism and is responsive to growth factors, cellular energy status, and nutrient availability, mTOR inhibitors, such as rapamycin, were highly effective in PKD rodent models but failed in subsequent clinical trials, most likely due to dose-limiting, significant extra-renal side effects and toxicities.

As an alternative to pharmacological intervention, modulation of mTOR activity in the kidney via dietary intervention was explored, since mTOR is under control of nutrient availability. As reported in Kipp, et al. (2016). A mild reduction of food intake slows disease progression in an orthologous mouse model of polycystic kidney disease. Am. J. Physiol. Renal Physiol. 310, F726-F731, a very mild reduction in food intake, by only 23%, profoundly inhibited renal cyst growth and mTOR activity while not affecting body weight gain. Another study, using two different orthologous mouse models, had similar conclusions and showed that food restriction by 40%, and even by only 10%, significantly inhibited renal cyst growth, as reported in Warner, et al., (2016). Food restriction ameliorates the development of polycystic kidney disease. J. Am. Soc. Nephrol. 27, 1437-1447. These results raise questions about the mechanism underlying the beneficial effect of dietary restriction, including whether the inhibition of renal cyst growth was due to overall caloric restriction or due to the restriction of a particular macro- or micro-nutrient, or by a different mechanism entirely.

As set forth herein, dietary restriction strongly inhibits renal cyst growth due to metabolic changes caused by intermittent fasting. Time-restricted feeding, in comparison to isocaloric ad libitum feeding, causes an intermittent decrease of blood glucose and an increase in ketogenesis and leads to strong inhibition of renal cyst growth, proliferation, and fibrosis. These effects are not merely due to circadian feeding rhythm because ad libitum administration of a ketogenic diet (KD) similarly inhibits renal cyst growth. Herein is shown that acute fasting in mouse, rat, and feline models of PKD induces significant apoptosis in cyst-lining epithelial cells and a striking reversal of renal cystic burden. Finally, it is shown herein, surprisingly, that supplementation of diet with just the natural ketone BHB replicates the beneficial effects of dietary restriction. These results indicate that dietary restriction has profound inhibitory effects on PKD progression, and this depends on induction of ketosis, as renal cyst cells in PKD appear to be metabolically inflexible and thus unable to adapt to alternative fuel sources. These results demonstrate that disease progression in ADPKD can be controlled by dietary interventions such as time-restriction or KDs and also, unexpectedly, by BHB supplementation or treatments that replicate BHB action.

Glucose Levels Predict the Rate of Kidney Volume Change in Individuals with ADPKD. Individuals with ADPKD and type 2 diabetes have significantly larger total kidney volume (TKV) than those with ADPKD alone, and overweight or obesity associates with faster progression in early-stage ADPKD. To investigate whether serum glucose levels even in normoglycemic, serum glucose was explored in a cohort of human ADPKD subjects with preserved renal function. Baseline serum glucose in this cohort uniquely predicted a greater TKV and htTKV increase over time. Similar analyses found no effect of the baseline serum glucose on average yearly change in GFR. Together, these results suggest that glucose availability may directly affect renal cystic disease progression in ADPKD and that limiting glucose availability may ameliorate cystic progression in PKD.

Figures 2A, 2B, 2C:
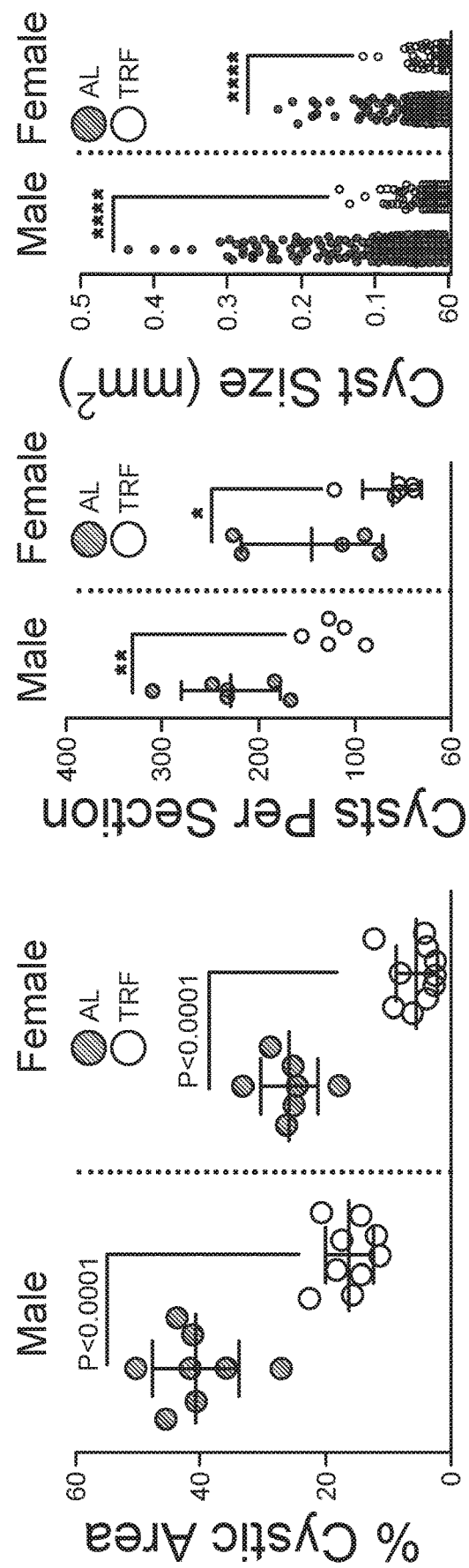
FIGS. 2A, 2B, and 2C depict the effects of time-restricted feeding in a PKD rat model.

Han:SPRD rats, a non-orthologous model of PKD with a mutation in Anks6 were placed on a time-restricted feeding (TRF) regime wherein TRF animals had access to food for an 8-h period within their 12-h dark cycle. Animals were treated for 5 weeks from post-natal weeks 3-8. TRF animals consumed a comparable number of calories and gained weight similar to the AL controls, indicating that TRF does not lead to food or caloric restriction, and there were no negative effects measured on any other organ. After 5 weeks of this dietary regimen, animals in the TRF cohort exhibited strikingly reduced renal cystic disease progression compared to animals in the AL cohort. Kidneys of TRF-treated animals were significantly less cystic (FIG. 2A) with a marked reduction in the 2-kidney/body weight ratio and improved kidney function as indicated by normalization of serum creatinine. In whole kidney sections, total cyst number (FIG. 2B) and cyst size (FIG. 2C), were decreased in TRF animals compared to controls, demonstrating that TRF inhibited both cystogenesis and cyst expansion. Additionally, TRF-treated animals had increased levels of BHB and reduced blood glucose indicative of ketosis.

Figure 3:
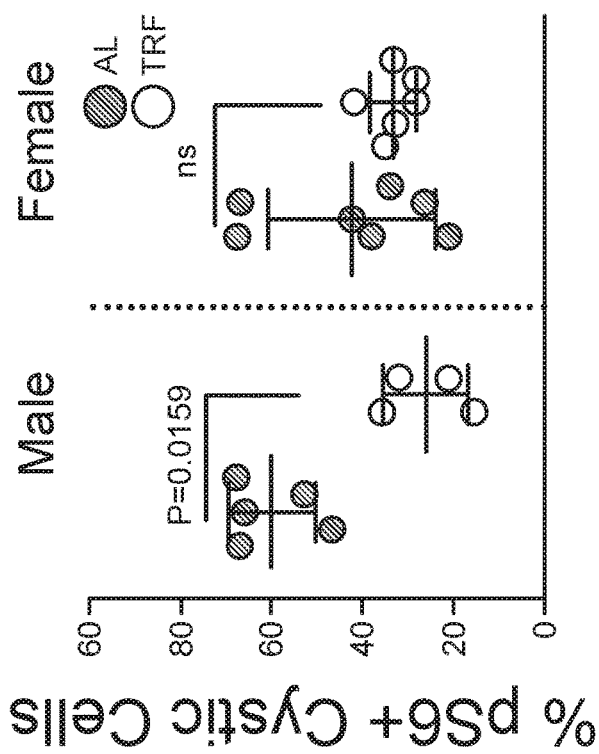
FIG. 3 depicts the abundance of pS6-positive cells in cyst-lining epithelia as a percent of the total number of DAPI-stained nuclei PKD rats on AL diet TRF diet.

TRF Reduces mTORC1 and STAT3 Signaling, Interstitial Fibrosis, and Proliferation in Cystic Kidneys. Changes in known PKD associated pathways and pathologies were assessed. A significant reduction in phosphorylated $S6^{S235/236}$ (FIG. 3) a downstream target in the mTOR pathway, was observed in cyst-lining epithelial cells of TRF-treated male, but not female, Cy/+ animals indicating inhibition of mTORC1 activity. PKD is known to lead to interstitial fibrosis, a hallmark of progressive renal disease. Collagen deposition was markedly reduced in TRF compared to AL animals. Myofibroblasts were strongly reduced and frequently absent in kidneys of TRF animals. Staining with the cell cycle marker Ki-67 revealed a significant reduction in cyst-lining cells in TRF compared to AL animals, indicating inhibition of proliferation. Active, phosphorylated STAT3, which has previously been shown to be activated in PKD and drives cystic progression, was reduced or absent in cysts in TRF-treated animals.

Figure 4A:
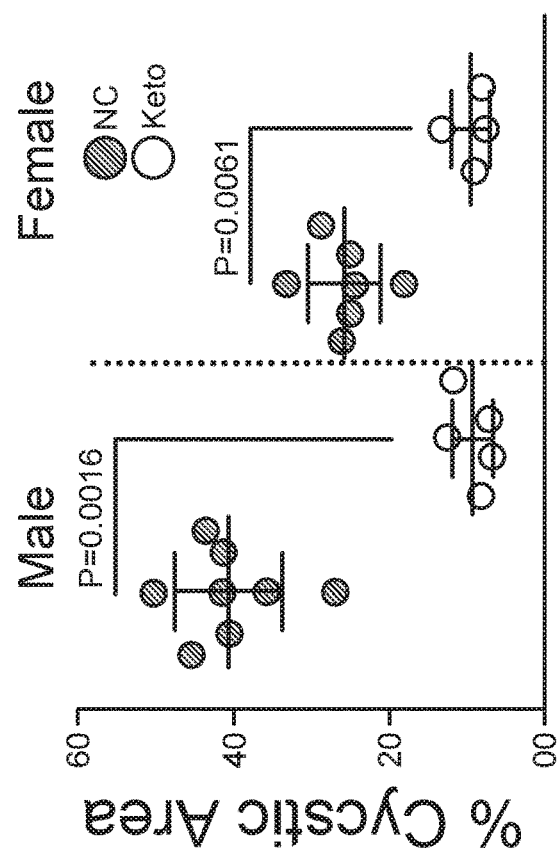
FIGS. 4A, 4B, 4C, 4D, and 4E depict the effects of a ketogenic diet on disease progression in juvenile Han:SPRD rats.
Figure 4D:
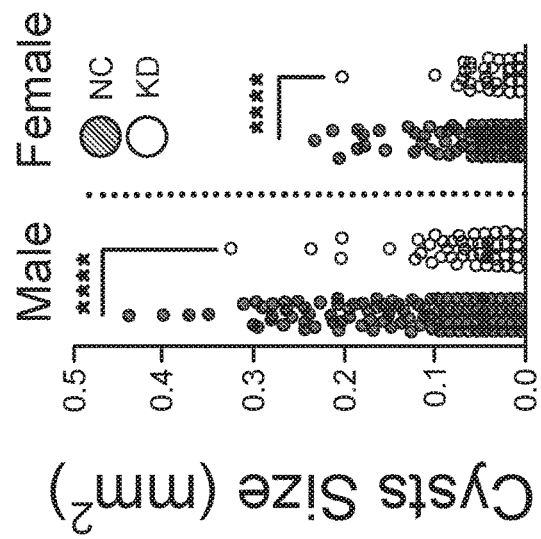
Figure 4C:
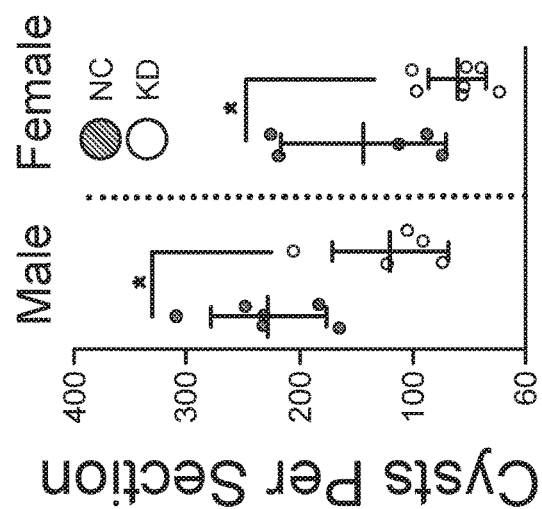
Figure 4B:
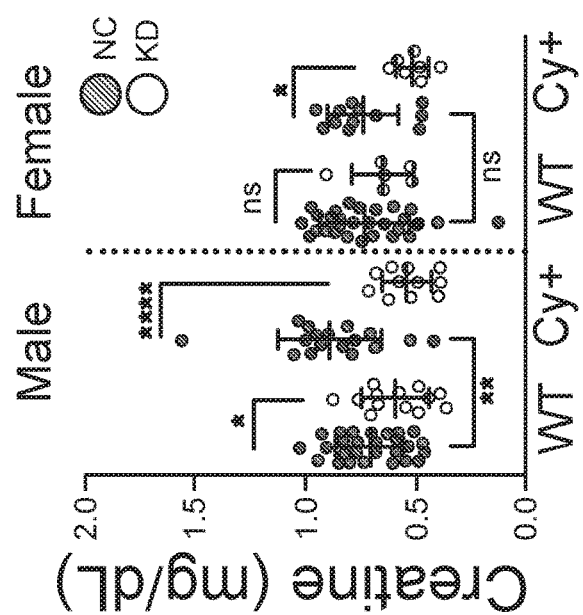

A KD Ameliorates Disease Progression in Juvenile Han: SPRD Rats. Han:SPRD rats were given ad libitum access to a high-fat, very-low-carbohydrate keto diet (KD—caloric ratio of 91% fat, 2% carbohydrates, and 5% protein) and compared to animals with ad lihbitum access to NC (caloric ratio of 62% carbohydrates, 25% protein, and 13% fat). Animals were treated again for 5 weeks from post-natal weeks 3-8. Renal cystic disease progression was strongly inhibited in animals on the KD regimen compared to those on NC along with a remarkable reduction in the 2-kidney to body weight and cystic area (FIG. 4A). KD-treated rats exhibited decreased blood glucose and increased BHB levels compared to NC controls, and the level of ketosis was more profound than that achieved with the TRF regimen. Animals on the KD appeared phenotypically normal and did not exhibit any signs of distress during the study. However, KD-treated animals exhibited reduced body weight gain, and only gained approximately 2%-10% of their body weight each week during the study. This lack of growth was not dependent on caloric intake, as the KD group consumed comparable calories to NC controls relative to their body weight, likely resulting from protein restriction. KD had a disproportionate inhibitory effect on the growth of polycystic kidneys as compared to normal kidneys. Importantly, KD feeding led to improved kidney function (FIG. 4B) as well as inhibited both cystogenesis (FIG. 4C) and cyst expansion (FIG. 4D).

Figure 5A:
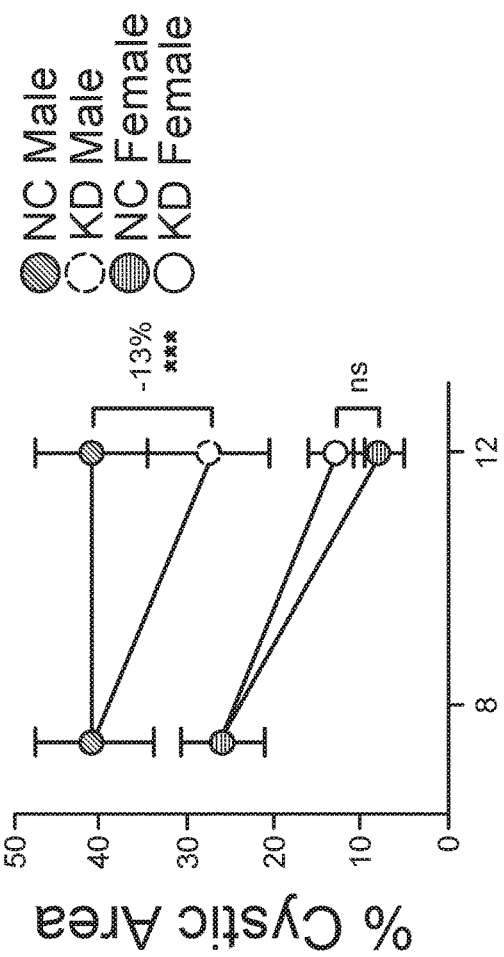
FIGS. 5A, 5B, and 5C depict PKD progression in rats treated with keto diet.
Figure 4E:
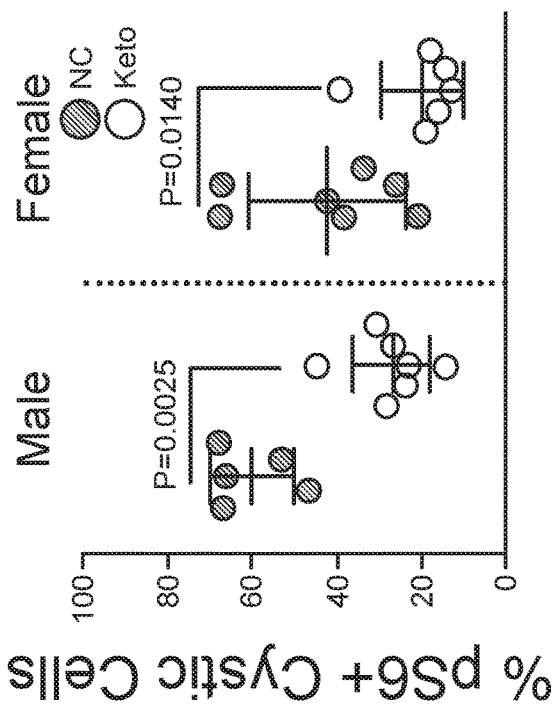
Figure 5C:
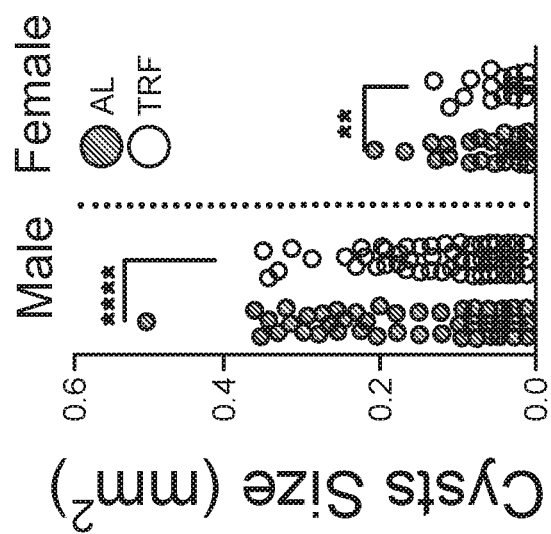
Figure 5B:
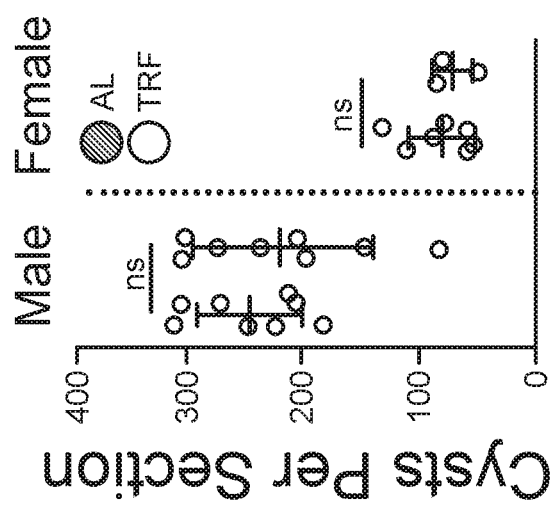
Figure 6B:
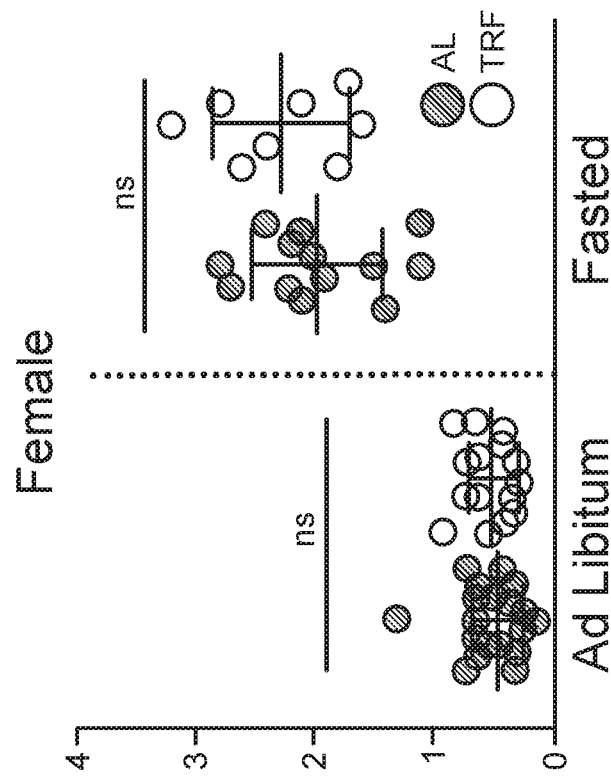
FIGS. 6A, 6B, and 6C depict effects of fasting (acute 48-h fast) in Han:SPRD and WT rats.
Figure 6A:
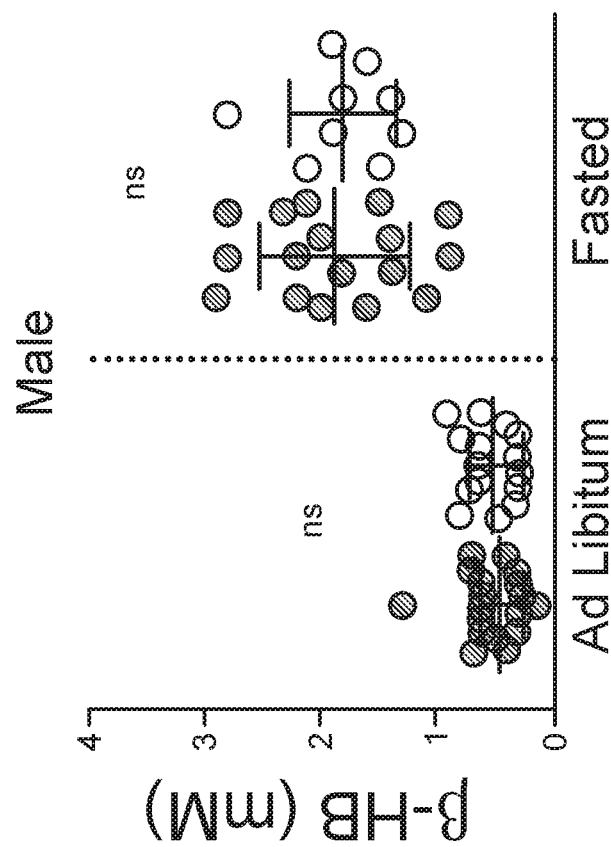
Figure 6C:
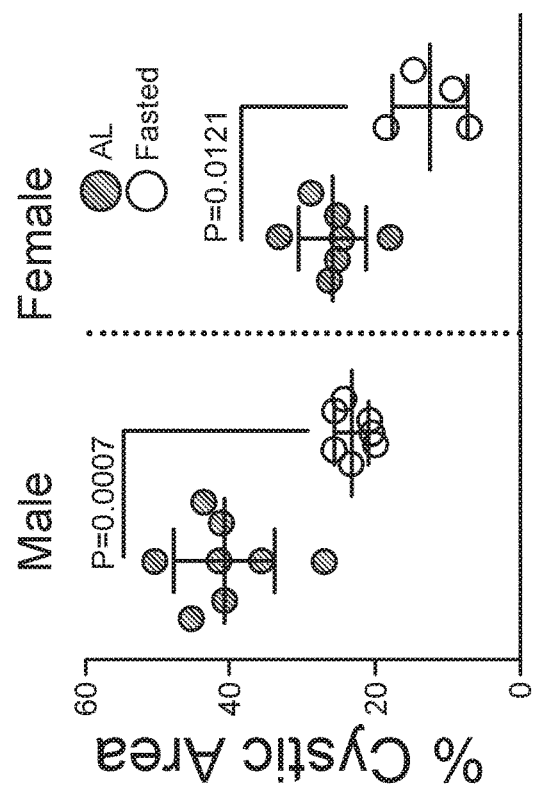

The effects of KD treatment on PKD progression were generally similar to those caused by the TRF treatment, mTOR (FIG. 5) and STAT3 activity in cystic epithelia were both blunted in KD-fed rats. SMA1-positive myofibroblasts were less in KD-fed animals compared to NC controls and was accompanied by a decrease in collagen deposition and the percent of Ki-67-positive demonstrating inhibition of cell cycle entry and proliferation (FIG. 6A). It was also found that KD feeding increased the levels of phospho-AMPK in the kidneys of cystic animals and increased CPT1a levels in male cystic, but not female cystic, rats (FIGS. 6B and 6C).

A KD Ameliorates Disease Progression in Adult Han: SPRD Rats. Han:SPRD rats at an older age (post-natal week 8-12) were fed KD versus NC. At this age, there is no longer cystic kidney enlargement, and no further change in kidney size was observed. During the treatment period, weight gain was mildly affected in rats on the KD, and there was no difference between wild-type and cystic animals. In contrast, the total mass of polycystic kidneys remained nearly the same in animals on NC but lowered by 35% in male rats on KD, accompanied by diminished 2-kidney to body weight ratio and percent cystic area (FIG. 6A). Similar to the juvenile experiments, the KD again affected the organ size of polycystic kidneys disproportionally because wild-type kidneys or other organs, such as the heart, were largely unaffected. Unlike the juvenile experiments, serum creatinine was unaffected by KD treatment in adult rats as was the total number of cysts per animal (FIG. 6B). There was, however, a marked reduction in cyst size (FIG. 6C), indicating that KD feeding prevents cyst growth in animals at that age. KD feeding led to a reduction in fibrosis in male animals, as indicated by reduced collagen, but there was no detectable difference in myo-fibroblasts, mTOR activity, or the cell cycle marker Ki-67.

Figure 7:
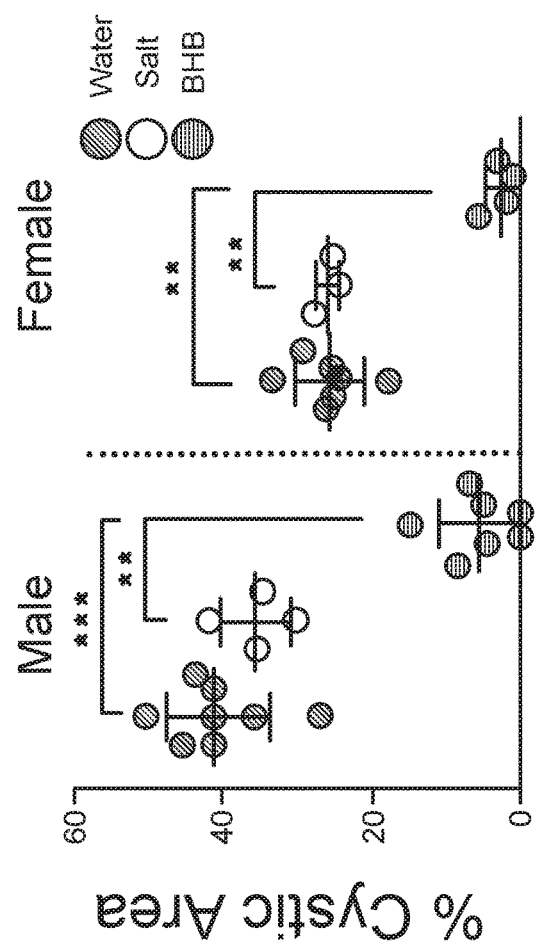
FIG. 7 depicts the cystic index (percent cystic area) in Han:SPRD PKD rats administered BHB, vs. control rats given water or water with salt equivalent to the BHB treatment.

Acute Fasting Leads to Cell Death and Renal Cyst Regression in Multiple PKD Animal Models. The strong inhibitory effects on PKD progression was observed with ketosis induced by TRF and KD regimens during the course of several weeks. To investigate whether ketosis has any fast-acting effects on renal cysts, Han:SPRD rats were subjected to acute ketosis via fasting. 8-week-old animals were fasted for 48 h with free access to water. As expected, acute fasting led to decreased blood glucose and increased blood BHB values (FIGS. 7A and 7B), indicating the induction of ketosis. The fasting-induced modest decrease in body weight (12%) is expected due to depletion of fat and glycogen reserves, primarily in adipose tissue, liver, and skeletal muscle, respectively, and was consistent between wild-type and cystic animals. Strikingly, acute fasting strongly affected cystic kidneys, leading to a 20% reduction in cystic area (FIG. 7C) and a concurrent reduction in kidney mass and the 2-kidney/heart weight ratio. Fasting had minimal-to-no effect on the weight of hearts and normal kidneys as expected, indicating that the fasting effects are specific to PKD kidneys. The loss of mass was not due to any loss of glycogen, and the reduction of cystic volume accounted for the observed loss in kidney mass, demonstrating that acute fasting leads to a loss of cyst fluid.

TUNEL staining revealed that acute fasting led to greater cell death of cystic cells but did not cause greater cell death in normal, non-cystic kidneys. In particular, there was a conspicuous number of TUNEL-positive, detached cells in cyst lumens, indicating that these dead cells originated from sloughed-off cyst-lining cells. Renal cysts in fasted animals frequently exhibited fragmented cells and denuded epithelium, which was not observed in renal cysts of control-fed cystic animals, demonstrating that loss of cyst fluid caused by acute fasting is due to cell death and disruption of the epithelial barrier of cysts, leading to draining of cyst fluid, presumably via the interstitium and lymphatics, leading to overall shrinking of polycystic kidneys.

Next was explored the possibility that increased supply of fatty acids during ketosis may affect cystic cells. As expected, intracellular oil droplets are rarely observed in normal or cystic kidneys in control-fed animals while acute fasting leads to accumulation of oil droplets in tubule cells in normal kidneys consistent with previous reports. Cyst-lining cells in polycystic kidneys exhibited a much exaggerated degree of cytoplasmic oil droplet accumulation. Frequently, most of the cytoplasm of the affected cells appeared to be occupied by oil droplets suggesting a state of severe steatosis. These findings demonstrate that cyst-lining cells have the ability to take up circulating fatty acids during acute fasting but are unable to sufficiently metabolize them, leading to lipotoxicity and greater cell death.

To test acute ketosis in an orthologous mouse model of PKD, the orthologous Pkd1:Nestin-Cre model was used. Fasting for 24 h, with free access to water, led to a pronounced decrease in blood glucose and increase in blood BHB but no significant change in kidney mass or 2-kidney to body weight. TUNEL staining revealed that acute fasting induced apoptotic cell death in cyst-lining cells and greater TUNEL-positive luminal cells, in polycystic kidneys but not in normal kidneys. It is speculated that the short duration of fasting in mice is insufficient to lead to significant cyst draining and a measurable effect on cystic burden, as compared to rats.

Figure 8A:
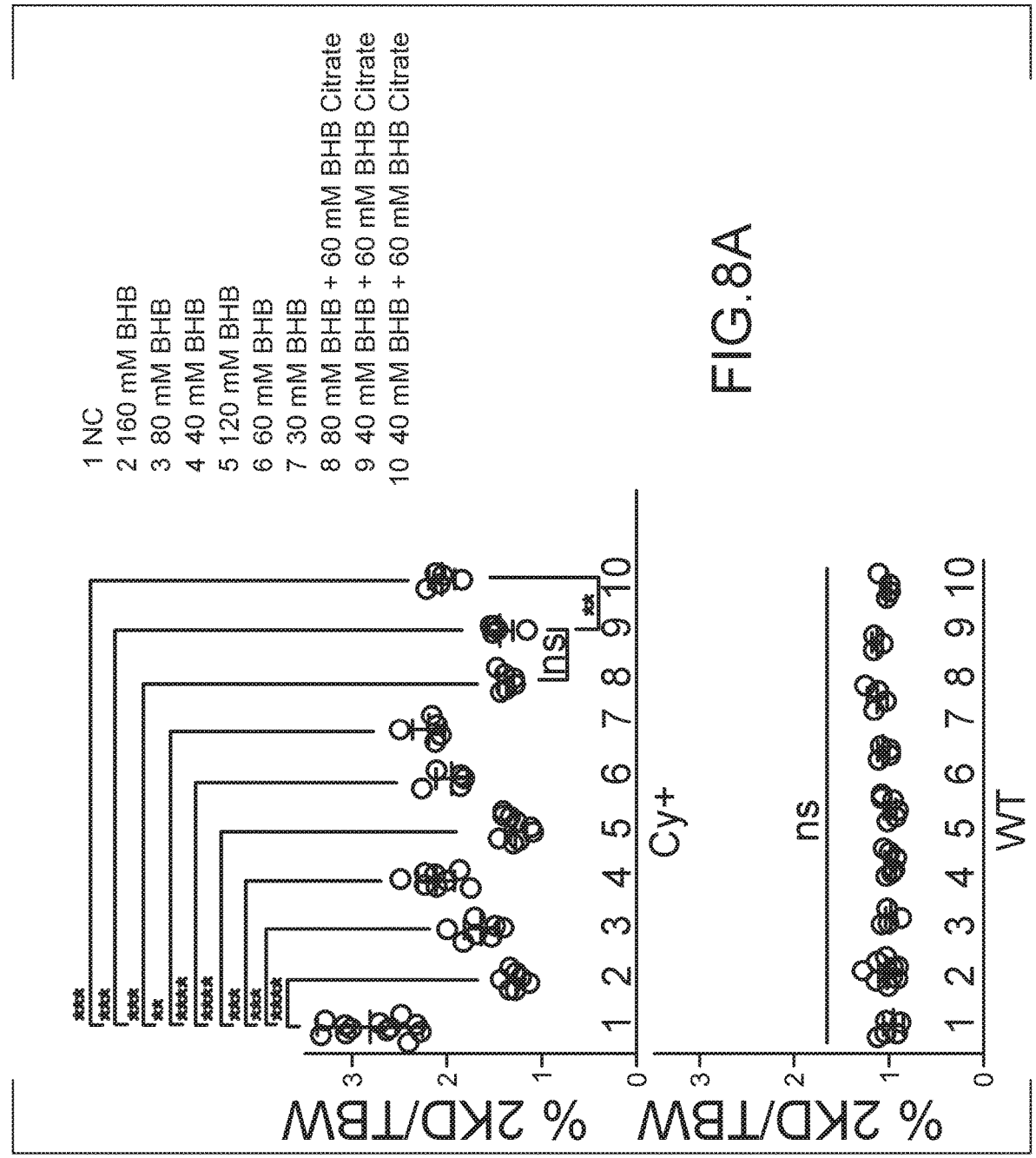
FIGS. 8A and 8B depict the effects of varying concentrations of BHB and citrate, as well as BHB-citrate combination treatments, in PKD rats.

Oral BHB Treatment Prevents Polycystic Disease Progression in Juvenile Rats. To investigate if BHB might affect PKD progression, Han:SPRD rats were treated with BHB from post-natal weeks 3-8 in the context of ad libitum feeding with normal, high-carbohydrate chow (NC). BHB was administered as a sodium and potassium salt in the drinking water ad libitum at a dose equivalent to that recommended as a dietary supplement in BHB supplement drinks. Control cohorts received either normal water or water supplemented with the molar equivalents of salt provided in the BHB supplement (a mixture of NaCl/KCl). All treated animals consumed comparable amounts of water and calories, and BHB treatment had no effect on body weight or blood glucose levels. Surprisingly, after 5 weeks of treatment with BHB, the kidneys of PKD animals were nearly indistinguishable from kidneys of wild-type animals, both at the gross and histological level. BHB-treated PKD rats showed striking and unexpected reductions in the 2-kidney to body weight ratio and the cystic area (FIG. 8A) compared to water- and salt-treated controls. Neither wild-type kidneys nor other organs were affected by BHB treatment, indicating that the effect is specific to polycystic kidneys. Surprisingly, BHB treatment led to a strong reduction in fibrosis, almost complete elimination of myofibroblasts, improved kidney function (assessed by creatinine), and inhibition of proliferation.

These unexpected results demonstrate that BHB acts in a dominant fashion as a suppressor of PKD progression, even in animals that are fed a high-carbohydrate diet and have unaltered blood glucose levels. Altogether, our results demonstrate that inducing a state of ketosis, either by dietary intervention or surprisingly even by mimicking its effects with BHB, is an effective treatment for ADPKD in humans. A common factor in all of the interventions described herein was the elevation of BHB. Remarkably, treatment with BHB alone, even in the context of a normal high-carbohydrate rodent diet proved to be highly effective. Unexpectedly, this demonstrates that BHB itself is a major factor in suppressing PKD progression.

The results also demonstrate that ketosis strongly inhibits not only renal cyst growth but also fibrosis. During the progression of PKD, cyst proliferation and fibrosis typically go hand in hand, and it is possible that both processes may reinforce each other. Myofibroblasts have been shown to be abundant in PKD kidneys and are thought to be a major contributor to fibrosis. Herein was demonstrated that ketosis greatly and unexpectedly reduces the abundance of pericystic myofibroblasts, especially the TRF regimen and BHB treatment, to almost complete absence. Consequently, overall fibrosis, as measured by collagen deposition, is strongly reduced.

Most individuals with ADPKD in industrialized societies consume a high-carbohydrate diet throughout their waking hours and only rarely, if ever, experience periods of ketosis. A recent nutritional feasibility study recommends high-carbohydrate diets for individuals with ADPKD, as reported in Taylor, et al. (2017). Diet and polycystic kidney disease: a pilot intervention study. Clin. Nutr. 36, 458-466, as do many available cookbooks, websites, online forums, etc., where individuals with ADPKD may seek dietary advice. The results provided herein suggest that such dietary habits may worsen PKD progression. In contrast, moderation in caloric intake has been recommended for the management of ADPKD, as reported in Chebib, and Torres (2018). Recent advances in the management of autosomal dominant polycystic kidney disease. Clin. J. Am. Soc. Nephrol. 13, 1765-1776. The results presented herein, however, demonstrate that reducing caloric intake per se would not necessarily lead to inhibition of cystic progression but that the induction of the state of ketosis is instead important, irrespective of caloric intake.

Figure 8B:
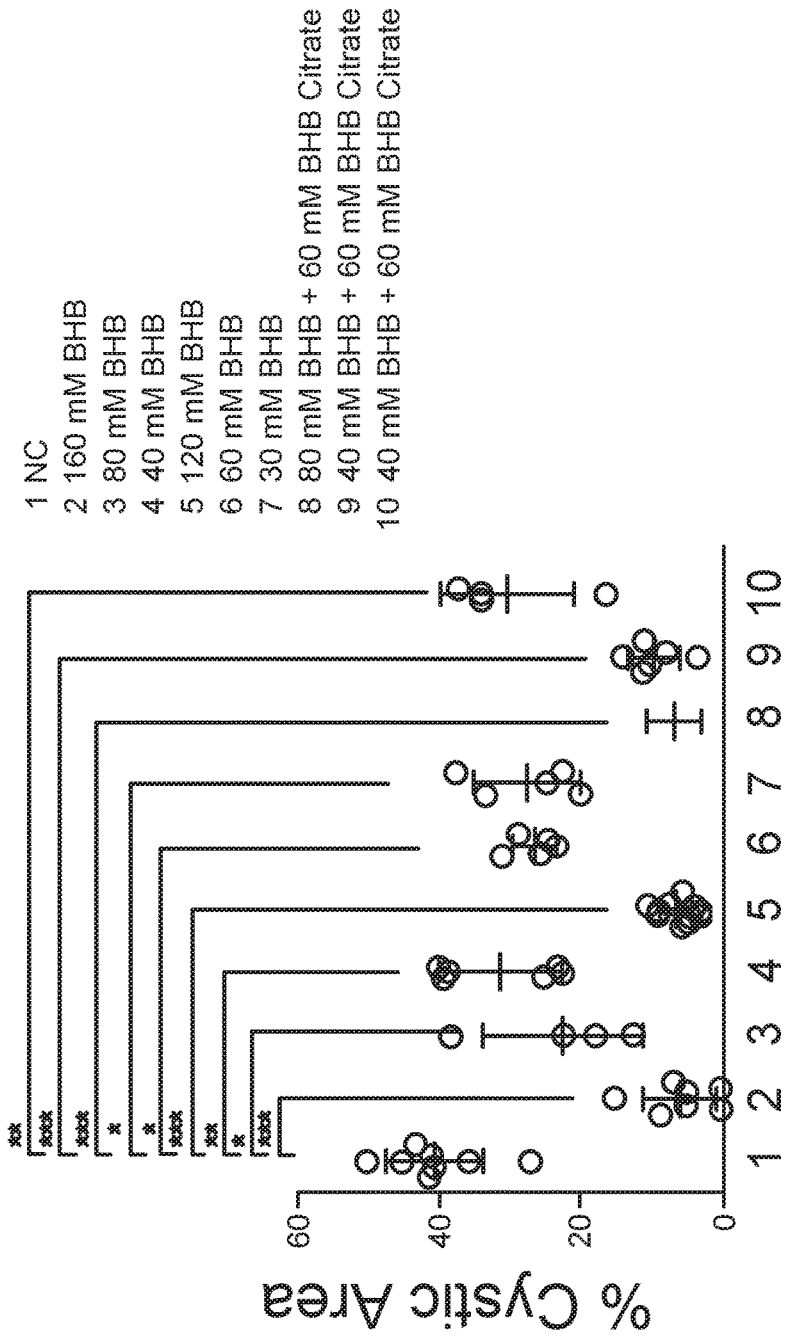

Example 2. Co-Administration of BHB and Citrate Ameliorate Renal Cyst Growth in Polycystic Kidney Disease To investigate BHB, citrate, and combined BHB and citrate effects on PKD progression, Han:SPRD rats were treated with BHB or a combination of BHB and citrate from post-natal weeks 3-8 in the context of ad libitum feeding with normal, high-carbohydrate chow (NC). In the BHB treatments, BHB was administered as a sodium and potassium salt in the drinking water ad libitum at a dose equivalent to that recommended as a dietary supplement in BHB supplement drinks. In the citrate treatments, citrate was administered as a combination of tripotassium citrate and citric acid at a (0.82/1) ratio at a dose equivalent to that recommended utilized in citrate dietary supplements. Control cohorts received either normal water or water supplemented with the molar equivalents of salt provided in the BHB or BHB-citrate supplements (a mixture of NaCl/KCl). Control cohorts received either normal water or water supplemented with the molar equivalents of salt provided in the BHB or BHB-citrate supplements (a mixture of NaCl/KCl). All treated animals consumed comparable amounts of water and calories, and BHB treatment had no effect on body weight or blood glucose levels. After 5 weeks of treatment with BHB or BHB citrate, the kidneys of PKD animals were nearly indistinguishable from kidneys of wild-type animals both at the gross and histological level. BHB or BHB-citrate treated PKD rats showed striking reductions in the 2-kidney to body weight ratio (FIG. 8A) and the cystic area (FIG. 8B) compared to water- and salt-treated controls. Neither wild-type kidneys nor other organs were affected by BHB treatment, indicating that the effect is specific to polycystic kidneys.

The results demonstrate dose-dependent benefits of BHB, and similar dose-dependent therapeutic effects from citrate, particularly at the 120 mM dosage. These results also demonstrate that the combination of BHB with citrate provides a synergistic response in PKD rats, even achieved at lower dosages of both BHB and citrate.

Example 3. GPR109A Activation in PKD

Figure 9:
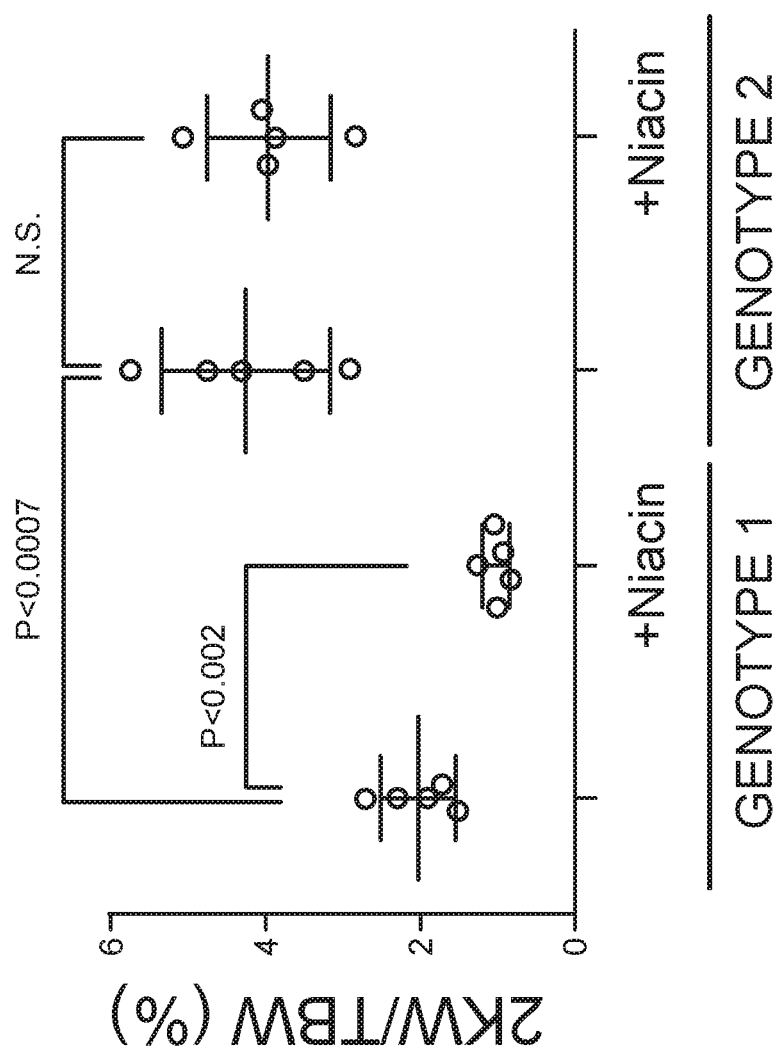
FIG. 9 depicts PKD progression (as assessed by 2-kidney to total body weight ratio) in niacin-treated PKD mice that express GPR109A (Genotype 1), and in GPR109A knockout PKD mice (Genotype 2).

The results described above led to the unexpected conclusion that BHB has a strikingly strong dominant inhibitory effect on PKD progression. The most immediate and likely assumption would be that BHB may act by virtue of its property as a metabolite that is taken up by cells and used for energy generation. However, further experimentation led to unexpected results suggesting that this model is incorrect. Instead, the results surprisingly suggest that the beneficial action of BHB as an inhibitor of PKD progression is due to the activation of a specific receptor termed GPR109A. GPR109A is a member of the class of G-protein coupled receptors. It has recently been identified as the niacin receptor and it mediates the lipid-lowering effects of niacin due to its activation on adipocytes. It has been found that GPR109A is not only activated by niacin but also by high concentrations of BHB such as may occur during fasting-induced ketosis. The inventors of the present disclosure speculated that GPR109A may be expressed on cells in the kidney and that treatment with BHB would lead to its activation and affect PKD progression. To test this, GPR109A knockout mice were crossed with a PKD model. In these mice, the loss of GPR109A surprisingly indeed led to accelerated PKD progression, indicating that GPR109A is normally a suppressor if cyst growth. This is a novel finding that would have been unanticipated without the discoveries presented herein regarding the beneficial effect of BHB in ameliorating PKD progression. Additionally, treatment with niacin, a GPR109A agonist, ameliorates PKD progression in PKD mice expressing GPR109A but not in GPR109A knockout mice. For example, as presented in FIG. 9, PKD progression (as assessed by 2-kidney weight to total body weight ratio, 2 KW/TBW) was ameliorated by niacin treated PKD mice (10 mg/kg, daily ip, from postnatal day 8-21) that express GPR109A (Genotype 1), while niacin treatment had no beneficial effect on PKD progression in the GPR109A knockout mice (Genotype 2).

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

The invention claimed is:

1. A method of treating polycystic kidney disease, in a subject in need of treatment therefor, comprising
administering to the subject a therapeutic composition comprising a therapeutically effective amount of a ketonic composition, wherein the ketonic composition comprises BHB, a BHB analog, or a GPR109A agonist.

2. The method of claim 1,
wherein the ketonic composition comprises BHB.

3. The method of claim 1,
wherein the BHB analog comprises an ester of BHB.

4. The method of claim 1,
wherein the BHB analog comprises a precursor of BHB.

5. The method of claim 4,
wherein the precursor of BHB comprises 1,3-butanediol.

6. The method of claim 1,
wherein the therapeutically effective amount of the ketonic composition is an amount sufficient to recapitulate ketosis in the subject.

7. The method of claim 6,
wherein the ketonic composition is BHB or a BHB analog and wherein the therapeutically effective amount of the ketonic composition is an amount sufficient to increase blood BHB to at least 0.250 mMol BHB per liter of blood in the subject.

8. The method of claim 1, wherein
the ketonic composition comprises BHB; and
the ketonic composition is co-administered with a crystal precipitation inhibitor, in an amount sufficient to inhibit in vivo crystal formation.

9. The method of claim 8, wherein
the crystal precipitation inhibitor is a composition selected from the group consisting of citrate, hydroxycitrate, an ester of citric acid, an amide of citric acid, a composition that alkanizes urine, a carbonate or bicarbonate, magnesium carbonate or bicarbonate, calcium carbonate or bicarbonate, sodium carbonate or bicarbonate, allopurinol, oxypurinol, febuxostat, an inhibitor of xanthine oxidase, Lesinurad, Rasburicase, and a calcium chelator.

10. The method of claim 9,
wherein the crystal precipitation inhibitor comprises citrate, wherein the weight percentage of citrate in the therapeutic composition is at least 10%.

11. The method of claim 1,
wherein the therapeutic composition is administered orally.

12. The method of claim 11, wherein
the therapeutic composition comprises a dietary supplement.

13. The method of claim 11, wherein
the therapeutic composition comprises a food item.

14. The method of claim 1, wherein
the subject is a cat or dog having polycystic kidney disease.

* * * * *